US007335507B2

(12) United States Patent
Anzar et al.

(10) Patent No.: US 7,335,507 B2
(45) Date of Patent: Feb. 26, 2008

(54) PROCESS FOR THE STAINING OF SPERM

(75) Inventors: Muhammad Anzar, Chesterfield, MO (US); Cindy L. Ludwig, St. Louis, MO (US); Jeffrey A. Graham, Chesterfield, MO (US); Jeanette A. Glaenzer, University City, MO (US)

(73) Assignee: Monsanto Technology LLC, St. Louis, MO (US)

( * ) Notice: Subject to any disclaimer, the term of this patent is extended or adjusted under 35 U.S.C. 154(b) by 397 days.

(21) Appl. No.: 10/811,593

(22) Filed: Mar. 29, 2004

(65) Prior Publication Data

US 2005/0003472 A1    Jan. 6, 2005

Related U.S. Application Data

(60) Provisional application No. 60/458,731, filed on Mar. 28, 2003.

(51) Int. Cl.
*C12N 5/00* (2006.01)
*C12N 5/02* (2006.01)

(52) U.S. Cl. .......................................... 435/325; 435/2

(58) Field of Classification Search ............... 435/40.5, 435/2, 325
See application file for complete search history.

(56) References Cited

U.S. PATENT DOCUMENTS

| | | | |
|---|---|---|---|
| 3,005,756 A | 10/1961 | VanDemark et al. | |
| 3,791,384 A | 2/1974 | Richter et al. | |
| 4,267,268 A | 5/1981 | Nelson, Jr. et al. | |
| 4,362,246 A | 12/1982 | Adair | |
| 4,474,875 A | 10/1984 | Shrimpton | |
| 5,135,759 A * | 8/1992 | Johnson ....................... | 424/561 |
| 5,658,751 A | 8/1997 | Yue et al. | |
| 5,798,276 A | 8/1998 | Haugland et al. | |
| 5,985,216 A | 11/1999 | Rens et al. | |
| 6,071,689 A | 6/2000 | Seidel et al. | |
| 6,130,034 A | 10/2000 | Aitken | |
| 6,149,867 A | 11/2000 | Seidel et al. | |
| 6,263,745 B1 | 7/2001 | Buchanan et al. | |
| 6,309,815 B1 | 10/2001 | Tash et al. | |
| 6,316,234 B1 | 11/2001 | Bova | |
| 6,368,786 B1 | 4/2002 | Saint-Ramon et al. | |
| 6,372,422 B1 | 4/2002 | Seidel et al. | |
| 6,395,305 B1 | 5/2002 | Buhr et al. | |
| 6,524,860 B1 | 2/2003 | Seidel et al. | |
| 7,015,310 B2 * | 3/2006 | Remington et al. ......... | 530/350 |
| 2002/0119558 A1 | 8/2002 | Seidel et al. | |

FOREIGN PATENT DOCUMENTS

| | | |
|---|---|---|
| GB | 2145112 A | 2/1985 |
| WO | WO 99/33956 A1 | 7/1999 |
| WO | W 00/54026 A1 | 9/2000 |
| WO | WO 01/37655 A1 | 5/2001 |
| WO | WO 01/51612 A | 7/2001 |
| WO | WO 01/68110 A | 9/2001 |
| WO | WO 01/85913 A | 11/2001 |
| WO | WO 02/19594 A | 3/2002 |
| WO | WO 02/41906 A | 5/2002 |
| WO | WO 02/41906 A2 | 5/2002 |
| WO | WO 02/43574 A3 | 6/2002 |
| WO | WO 2004/087177 A | 10/2004 |
| WO | WO 2004/088283 A | 10/2004 |

OTHER PUBLICATIONS http://www.specialtymedia.com/05Resources/Protocols/ivfprotocol.htm.*
Salisbury et al, Journal of Reprodution and Fertility, vol. 6, 1963 p. 351-359.*
De Pauw et al, Biology of Reproduction, 2002, p. 1073-1079.*
Sabuer et al, Journal of Reproduction and Fertility vol. 120, 2000 p. 135-142.*
Culling, "Handbook of Histopathological and Histochemical Techniques," 3rd Ed., Butterworths, p. 192.
Johnson, U.S. Patent No. 5,135,759, File History.
Partsch, "Scrotal Temperature is Increased in Disposable Plastic Line Nappies," 2000, Arch Dis Child, V83, pp. 364-368.
Baumber, J., et al., "The Effect of Reactive Oxygen Species on Equine Sperm Motility, Viability, Acrosomal Integrity, Mitochondrial Membrane Potential, and Membrane Lipid Peroxidation," 2000, J. Andrology, vol. 21(6), pp. 895-902.
Bencic, D.C., et al., "Carbon Dioxide Reversibly Inhibits Sperm Motility and Fertilizing Ability in Steelhead (*Oncorhynchus mykiss*)," 2000, Fish Physiology and Biochemistry, vol. 23(4), pp. 275-281.
Boatman, D.E., et al., "Bicarbonate Carbon Dioxide Regulation of Sperm Capacitation Hyperactivated Motility and Acrosome Reactions," 1991, Biol of Reprod, vol. 44(5), pp. 806-813.
Bruemmer, J.E., et al., "Effect of Pyruvate on the Function of Stallion Spermatozoa Stored for up to 48 Hours," J Anim Sci, 2002, vol. 80 1), pp. 12-18.
Denniston, D.J., et al., "Effect of Antioxidants on the Motility and Viability of Cooled Stallion Spermatozoa," J. Reprod Fert Supp 56, 2001, pp. 121-126.
Garcia, M.A., et al., "Development of a Buffer System for Dialysis of Bovine Spermatozoa Before Freezing III. Effect of Different Inorganic and Organic Salts on Fresh and Frozen-Thawed Semen," 1989, Theriogenology, vol. 31(5), pp. 1039-1048.

(Continued)

Primary Examiner—Jon Weber
Assistant Examiner—Tiffany M. Gough
(74) Attorney, Agent, or Firm—Senniger Powers; Joseph A. Schaper

(57) ABSTRACT

Sperm cells are stained according to processes that involve the combining of sperm cells with a fluorescent DNA selective dye at an elevated temperature in excess of about 40° C. The methods allow for a decreased staining time. The cells may thereafter be efficiently sorted according to common separation methods, including flow cytometry.

38 Claims, 33 Drawing Sheets

OTHER PUBLICATIONS

Graves, C.N., et al., "Metabolism of Pyruvate by Epididymal-Like Bovine Spermatozoa," 1964, J Dairy Sci, vol. 47(12), pp. 1407-1411.

Graves, C.N., et al., "Metabolic End-products of Anaerobic Spermatozoan Metabolism," 1966, Nature, vol. 211, pp. 308-309.

Karow, A.M. et al., "Effects of Temperature, Potassium Concentration, and Sugar on Human Spermatozoa Motility: A Cell Preservation Model from Reproductive Medicine," 1992, Cryobiology, vol. 29, pp. 250-254.

Lodge, J.R., et al., "Carbon Dioxide in Anaerobic Spermatozoan Metabolism," 1968, J Dairy Sci, vol. 51(1), pp. 96-103.

Salisbury, G.W., Reversal by Metabolic Regulators of CO2-induced Inhibition of Mammalian Spermatozoa, 1959, Proc Soc Exp Biol Med, vol. 101(1), pp. 187-189.

Salisbury, G.W. et al., "Chapter 16: Extenders and Extension of Unfrozen Semen," Physiology of Reproduction and Artificial Insemination of Cattle, 2nd Ed., 1961, W.H. Freeman and Company, pp. 445 and 464.

International Search Report for PCT/US2005/010598 dated Jun. 27, 2005, 5 pgs.

International Search Report for PCT/US2004/010481 dated Oct. 10, 2005, 7 pgs.

International Search Report for PCT/US2005/010599 dated Dec. 12, 2005, 9 pgs.

Arndt-Jovin et al., "Analysis and Sorting of Living Cells According to Deoxyribonucleic Acid Content," Jour. Histochem. and Cytochem., 1977, 25(7), pp. 585-589.

D'Occhio, M., "Sexing of Sperm and Embryos: Use of Sexed Sperm in AI, IVF, ICSI and Graft," Animal Breeding Use of New Technologies, Chapter 19, pp. 247-264, Kinghorn, van der Werf and Ryan, Eds., date unavailable.

Dresser et al., "Analyses of DNA Content of Living Spermatozoa Using Flow Cytometry Techniques," Jour. Reprod. and Fert., 1993, 93, pp. 357-365.

Ericsson et al., "Flow Cytometric Evaluation of Cryopreserved Bovine Spermatozoa Processed Using a New Antiobiotic Combination," Theriogenology, 1990, 33(6), pp. 1211-1220.

Farrell et al., "Quantification of Bull Sperm Characteristics Measured by Computer-Assisted Sperm Analysis (CASA) and the Relationship of Fertility," Theriogenology, 1998, 49(4), pp. 871-879.

Foote et al., "Motility and Fertility of Bull Sperm in Whole Milk Extender Containing Antioxidants," Animal Repro. Sci., 2002, 71(1-2), pp. 13-23.

Garner et al., "Viability Assessment of Mammalian Sperm Using SYBR-14 and Propidium Iodide," Bio. of Reprod, 1995, 53, pp. 276-284.

Gordon et al., "Genetic Transformation of Mouse Embryos by Microinjection of Purified DNA," Proc. Natl. Acad. Sci., 1980, 77(12), pp. 7380-7384.

Guthrie et al., "Flow Cytometric Sperm Sorting: Effects of Varying laser Power on Embryo Development in Swine," Mol. Reprod. and Develop., 2002, 61(1), pp. 87-92.

Johnson et al., "Modification of a Laser-Based Flow Cytometry for High-Resolution DNA Analysis of Mammalian Spermatozoa," Cytometry, 1986, 7, pp. 268-273.

Johnson, L.A., "Sex Preselection in Swine: Altered Sex Ratios in Offspring following Surgical Insemination of Flow Sorted X- and Y-Bearing Sperm," Reprod. Dom. Anim., 1991, 26, pp. 309-314.

Johnson, L.A., "Sex Preselection by Flow Cytometric Separation of X and Y Chromosome-Bearing Sperm Based on DNA Difference: A Review," Reproduction, Fertility and Development, 1995, 7(4), pp. 893-903.

Johnson, L.A., "Advances in Gender Preselection in Swine," Jour. of Reprod. and Fert., Proceedings of the Fifth International Conference on Pig Reproduction, Suppl. 52, 1997, pp. 255-266.

Johnson et al., "Enhanced Flow Cytometric Sorting of Mammalian X and Y Sperm: High Speed Sorting and Orienting Nozzle for Artificial Insemination," Theriogenology, 1998, 49(1), p. 361.

Johnson et al., "Sex Preselection: High-Speed Flow Cytometric Sorting of X and Y Sperm for Maximum Efficiency," Theriogenology, 1999, 52, pp. 1323-1341.

Johnson, L.A., "Sexing Mammalian Sperm for Production of Offspring: the state-of-the-art," Anim. Reprod. Sci., 2000, 60-61, pp. 93-107.

Maxwell et al., "Chlortetracycline Abalysis of Boar Spermatozoa After Incubation, Flow Cytometric Sorting, Cooling, or Cryopreservation," Mol. Reprod. and Develop., 46, 1997 pp. 408-418.

Morell et al., "Sexing of Sperm by Flow Cytometry," The Veterinary Record, 1988, pp. 322-324.

Rath et al., "Production of Piglets Preselected for Sex Following In Vitro Fertilization with X and Y Chromosome-Bearing Spermatozoa Sorted by Flow Cytometry," Theriogenology, 1997, 47, pp. 795-800.

Salisbury and Graves, "Substrate-free Epididymal-like Bovine Spermatozoa," J. Reprod. Fertil., 1963, 6, pp. 351-359.

Seidel et al., "Artificial Insemination of Heifers with Cooled, Unfrozen Sexed Semen," Theriogenology, 1998 49(1), p. 365.

Seidel et al., "Insemination of Heifers with Sexed Sperm," Theriogenology, 1999, 52, pp. 1407-1420.

Seidel et al., "Insemination of Heifers with Sexed Frozen or Sexed Liquid Semen," Website www.cymbs.colostate.edu, Abstract, Jun. 3, 1999, 2 pages.

International Search Report for PCT/US2004/009903 dated Aug. 16, 2004.

Schenk, J.L., et al., "Cryopreservation of Flow-Sorted Bovine Spermatozoa," Theriogenology, 1999, 52, pp. 1375-1391.

International Search Report for PCT/US2005/026269 dated Dec. 2, 2005, 7 pages.

De Pauw, M.C., et al., "Sperm Binding to Epithelial Oviduct Explants in Bulls with Different Nonreturn Rates Investigated with a New in Vitro Model," 2002, Biol Reprod, V67, pp. 1073-1079.

Sabeur, K., et al., "Effects of Angiotensin II on the Acrosome Reaction in Equine Spermatozoa," 2000, J Reprod Fert, V120, pp. 135-142.

Millipore Specialty Media, IVF Protocol, http://www.specialtymedia.com/05Resources/Protocols/ivfprotocol.htm, 2005.

* cited by examiner

Comparison of Fluorescence Intensity of sperm stained with 20uM Hoechst 33342 at 39°C & 41°C Comparison of Fluorescence Intensity of sperm stained with 30uM Hoechst 33342 at 39°C & 41°C Comparison of IVOS %Motility and % Prog Mot @ 43°C of 300uM Hoechst 33342 Stained Sperm Comparison of IVOS %Motility and % Prog Mot @ 43°C of 350uM Hoechst 33342 Stained Sperm

US 7,335,507 B2

PROCESS FOR THE STAINING OF SPERM

CROSS-REFERENCE TO RELATED APPLICATIONS

This application is a nonprovisional of U.S. patent application Ser. No. 60/458,731 which was filed Mar. 28, 2003, which is hereby incorporated herein by reference in its entirety.

BACKGROUND OF THE INVENTION

The present invention generally relates to a staining process to enable sperm separation for the purpose of producing gender enriched sperm.

The fertilization of animals by artificial insemination (AI) and embryo transplant following in vitro fertilization is an established practice. In the livestock production industry, the ability to influence the reproductive outcome toward offspring having one or more desired characteristics has obvious advantages. By way of example, there would be an economic benefit in the dairy industry to preselect offspring in favor of the female sex to ensure the production of dairy cows. The separation of sperm into enriched populations of X and Y chromosome-bearing cells, known as gender enriched semen or gender enriched sperm, is one method of achieving preselected offspring.

Johnson et al. (U.S. Pat. No. 5,135,759) describe the separation of intact X and Y chromosome-bearing sperm populations according to DNA content using a flow cytometer/cell sorter into X and Y chromosome-bearing sperm enriched populations. As described, the sperm is combined with a DNA selective dye at a temperature of 30 to 39° C. for a period of 1 hour (39° C.) to 1.5 hours (30° C.). A flow cytometer is then used to measure the amount of fluorescent light given off when the sperm passes through a laser beam. Because the X chromosome-bearing sperm contains more DNA than the Y chromosome-bearing sperm, approximately 3 to 5% depending upon the species, the X chromosome-bearing sperm yields a greater intensity of fluorescent light than the Y chromosome-bearing sperm. Droplets containing single sperm of a predetermined fluorescent intensity are given a charge and electrostatically deflected into collection vessels. The collected, gender enriched sperm population, is then used for microinjection or artificial insemination.

Seidel et al. (WO 02/43574) also describe separation of sperm into gender enriched populations of X and Y chromosome-bearing cells using flow cytometry. Seidel et al. describe staining the cells at a temperature between 30° C. and 40° C.

Didion et al. (WO 02/41906) describe staining sperm cells at temperatures of about 17° C. to 30° C. According to Didion et al., these staining temperatures avoided certain effects which may result from staining at greater temperatures, such as reduced sperm viability and efficiency. Furthermore, it was believed that the lower temperature staining provided advantageous effects on sperm orientation during sorting.

SUMMARY OF THE INVENTION

Among the various aspects of the present invention is the provision of a relatively rapid and efficient method of staining sperm cells and the provision of such a process in which decreased periods are required for dye uptake, thereby decreasing the time that elapses between the time of semen collection and production of gender enriched populations of X and Y chromosome-bearing sperm cells.

Briefly, therefore, the present invention is directed to a process for staining sperm cells. The process comprises forming a staining mixture containing intact viable sperm cells and a DNA selective fluorescent dye, and subjecting the staining mixture to a temperature of at least about 40° C.

Other aspects of the invention will be in part apparent, and in part pointed out hereinafter.

DETAILED DESCRIPTION OF THE EMBODIMENTS

Figure 1A:
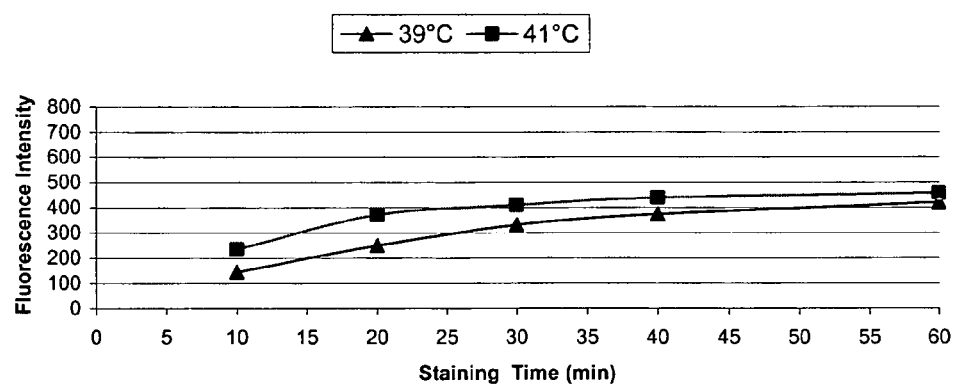
FIGS. 1A-1D graphically depict the results of the study carried out in Example 1 wherein fluorescence intensity of sperm is measured for sperm stained at varying concentrations of Hoechst 33342 dye at 39° C. and 41° C.
Figure 1B:
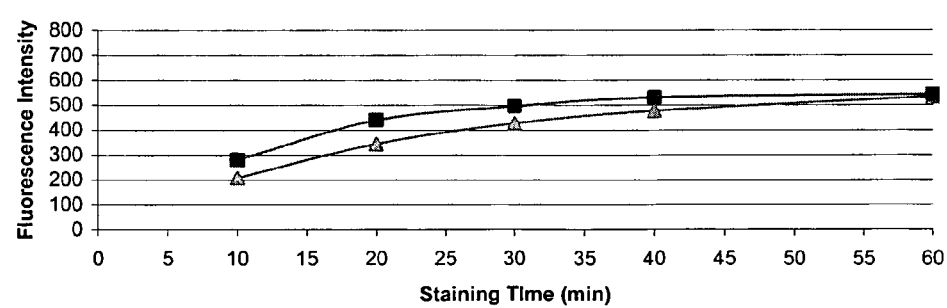
Figure 1C:
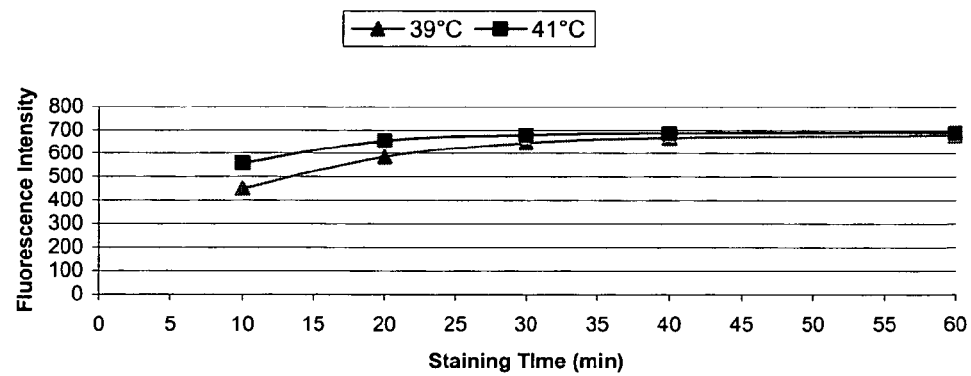
Figure 1D:
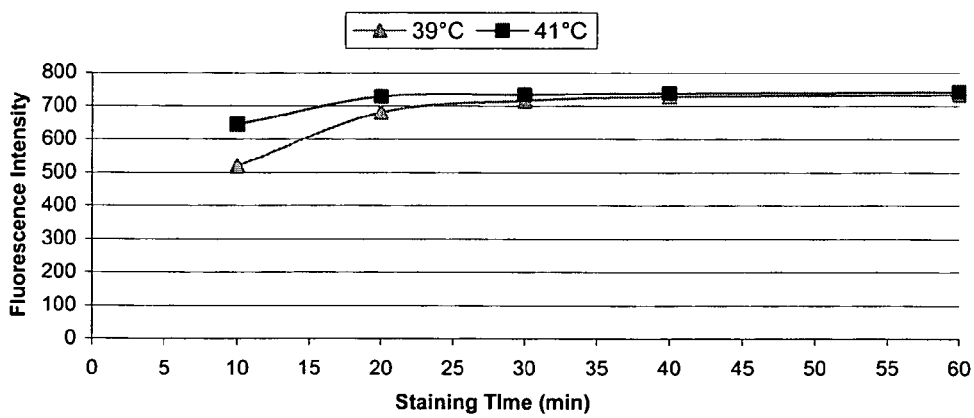
Figure 2A:
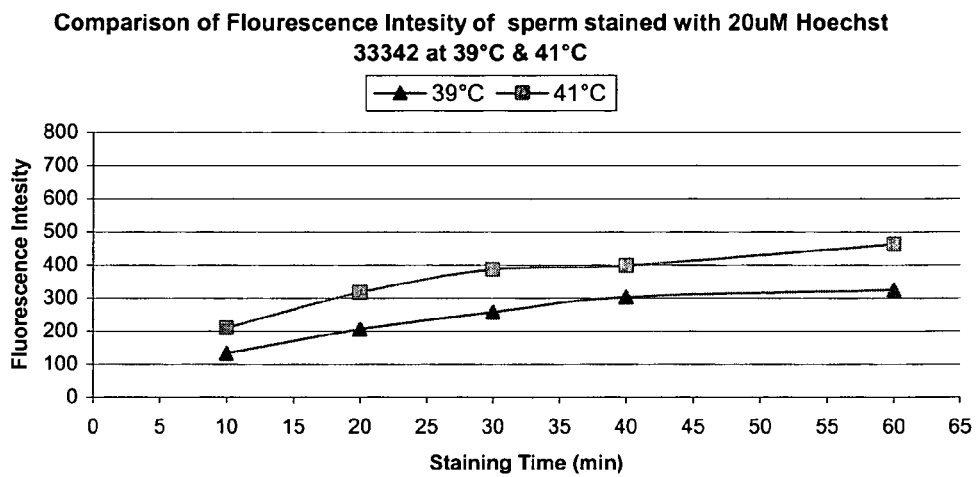
FIGS. 2A-2D graphically depict the results of the study carried out in Example 2 wherein fluorescence intensity of sperm is measured for sperm stained at varying concentrations of Hoechst 33342 dye at 39° C. and 41° C.
Figure 2B:
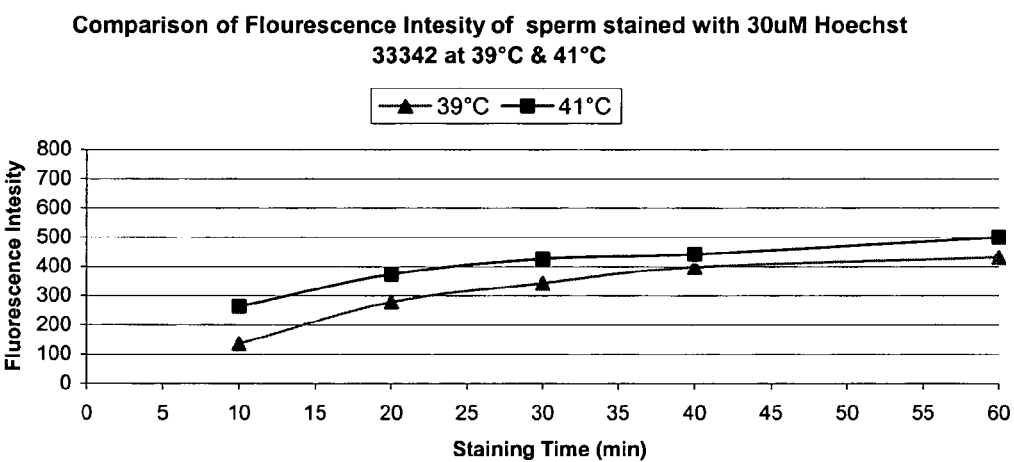
Figure 2C:
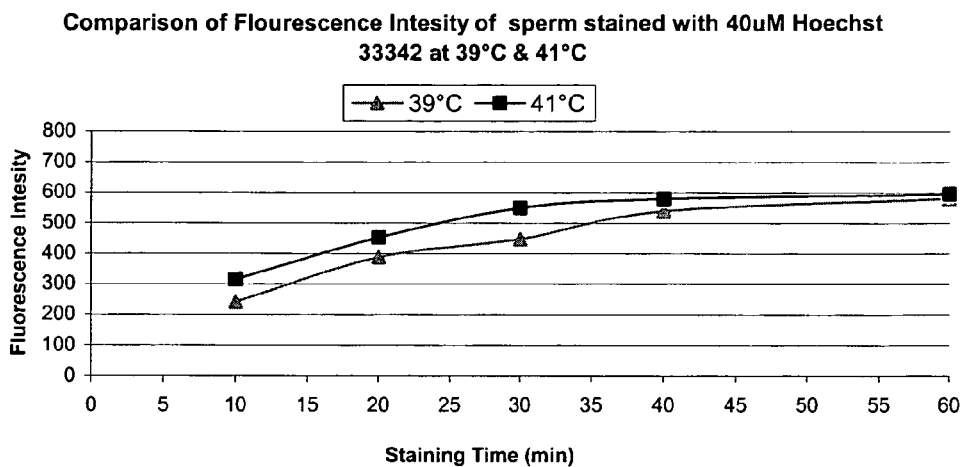
Figure 2D:
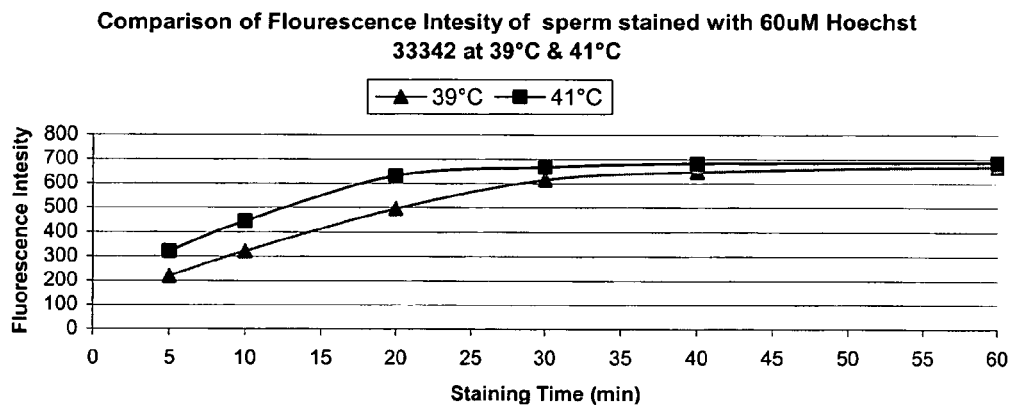
Figure 3A:
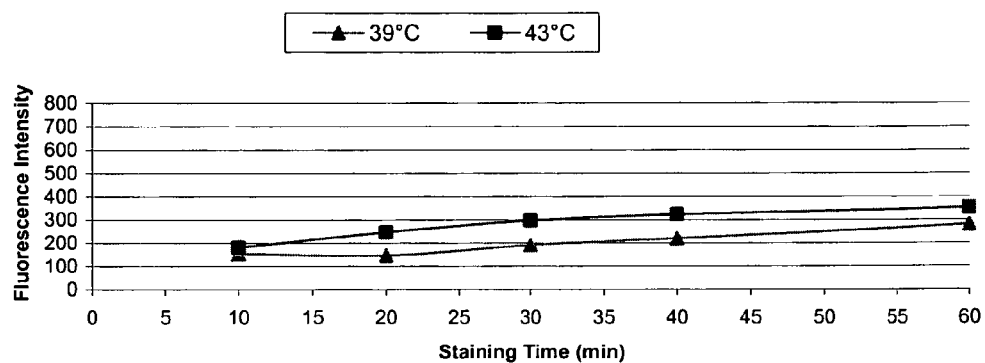
FIGS. 3A-3D graphically depict the results of the study carried out in Example 3 wherein fluorescence intensity of sperm is measured for sperm stained at varying concentrations of Hoechst 33342 dye at 39° C. and 43° C.
Figure 3B:
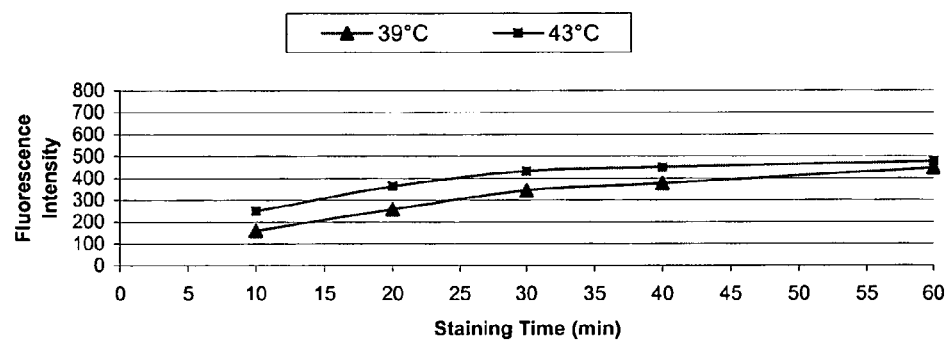
Figure 3C:
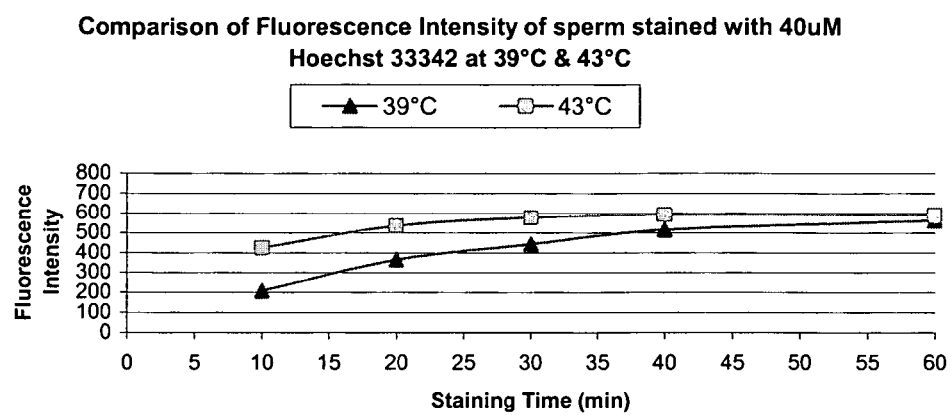
Figure 3D:
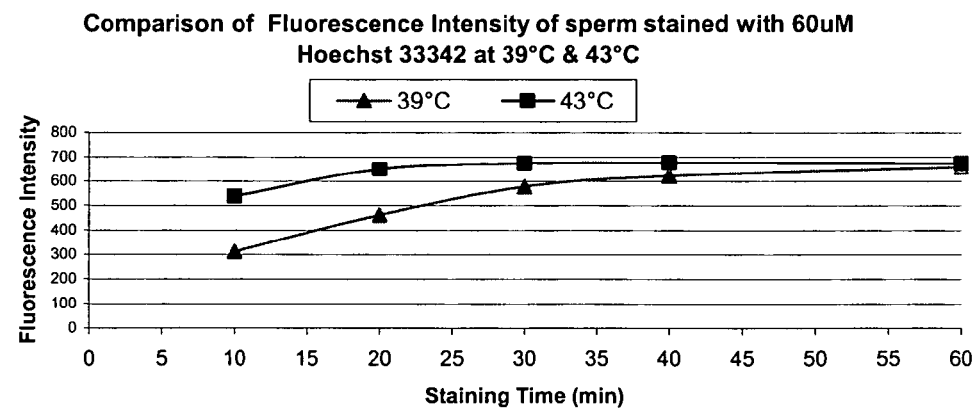

Surprisingly, it has been determined that sperm cells can be stained with a dye for use in flow cytometry processes at elevated temperatures, i.e., at temperatures in excess of 40° C., in less time than is required to stain the cells at lesser temperatures without significant impact upon sperm cell viability. In one embodiment, the sperm cells are exposed to the dye at a temperature of at least 41° C. In another embodiment, the sperm cells are exposed to the dye at a temperature of at least 42° C. In another embodiment, the sperm cells are exposed to the dye at a temperature of at least 43° C. In another embodiment, the sperm cells are exposed to the dye at a temperature of at least 44° C. In another embodiment, the sperm cells are exposed to the dye at a temperature of at least 45° C. In general, however, exposing the sperm cells to a temperature substantially in excess of 45° C. for any significant period of time may deleteriously affect the viability of the cells. Thus, in one embodiment, the sperm cells are exposed to the dye at a temperature of at least 41° C. but not in excess of 50° C. In another embodiment, the sperm cells are exposed to the dye at a temperature of at least 41° C. but not in excess of 48° C. In another embodiment, the sperm cells are exposed to the dye at a temperature of at least 41° C. but not in excess of 47° C. For example, in one presently preferred embodiment, the sperm cells are exposed to the dye at a temperature of at least 42° C. but not in excess of 47° C. By way of further example, in another presently preferred embodiment, the sperm cells are exposed to the dye at a temperature of at least 43° C. but not in excess of 45° C.

The process of the present invention may be used to stain intact, viable bovine, porcine, equine, or other mammalian sperm cells, derived from a freshly obtained semen sample or from a thawed cryopreserved semen sample. Various methods of collection of viable sperm are known and include, for example, an artificial vagina method or a gloved hand method. A typical bovine semen sample will contain about 0.5 to about 5 billion sperm cells per milliliter depending upon species and the particular animal within the species.

In general, sperm cells are stained in accordance with one aspect of the present invention by forming a staining mixture which comprises sperm cells and a DNA selective dye. Sperm cells are somewhat sensitive to significant changes in osmotic pressure and pH. To minimize impact upon sperm viability, therefore, it is generally preferred that the staining mixture be formed with these considerations in mind. Consistent with these considerations, the staining mixture may be formed in a variety of manners.

In one embodiment, neat semen is combined with the DNA selective dye. Thus, for example, dye in the form of a neat solid, including a free-flowing powder, or a liquid composition may be combined with neat semen. Alternatively, an unbuffered liquid in which the dye is dissolved or dispersed may be combined with neat semen. In each of these approaches, however, it is generally preferred that the formation of the staining mixture not cause the sperm to be subjected to a significant change in osmotic pressure or pH relative to neat semen sufficient to materially adversely affect their viability.

In another embodiment, neat semen is combined with a buffered liquid in which the dye is dissolved or dispersed to form the staining mixture. Advantageously, the buffer will aid in the avoidance of any significant change in osmotic pressure or pH relative to neat semen sufficient to materially adversely affect their viability as a consequence of the formation of the mixture.

In another embodiment, a sperm source is combined with a buffer to form a sperm suspension and the sperm suspension is thereafter combined with the dye to form the staining mixture. Suspending the sperm cells in a buffered liquid prior to contact with the dye can advantageously protect the sperm cells from significant changes in pH and osmotic pressure which would otherwise result from the addition of the dye. In this embodiment, the sperm source may be neat semen. Alternatively, the sperm source may be a sperm-containing semen derivative obtained by centrifugation or the use of other means to separate semen into fractions.

In another embodiment, the DNA selective dye is combined with a buffer, or is included as part of a buffer recipe, phates, citrates, acetates, and lactates. Such buffers may also contain a nutrient source, such as for example sugar, and/or an antibiotic, such as streptomycin. Preferred buffers include TCA, TEST, sodium citrate, TL, and HEPES. In certain embodiments of the invention, the semen sample is diluted with one or more of the buffer solutions described in Table I. For example, in one embodiment, the semen sample is diluted with a TCA#1 buffer solution having the composition described in Table I. In another embodiment, the semen sample is diluted with a TCA#2 buffer solution having the composition described in Table I. In another embodiment, the semen sample is diluted with a TEST buffer solution having the composition described in Table I. In another embodiment, the semen sample is diluted with a sodium citrate buffer solution having the composition described in Table I. In yet another embodiment, the semen sample is diluted with a TL buffer solution having the composition described in Table I. In another embodiment, the semen sample is diluted with a HEPES buffer solution having the composition described in Table I. In a further embodiment, the sperm cells may be diluted with a buffer solution comprising 0.204 g $NaHCO_3$, 0.433 g $KHCO_3$, and 0.473 g $C_6H_8O_7 \cdot H_2O$ per 25 mL of purified water (0.097 moles/L of $NaHCO_3$, 0.173 moles/L of $KHCO_3$, 0.090 moles/L $C_6H_8O_7 \cdot H_2O$ in water) to form a sperm suspension.

TABLE I

BUFFER RECIPES

| COMPONENTS | TCA#1 | TCA#2 | TEST | Na Citrate | HEPES | TL |
|---|---|---|---|---|---|---|
| Sodium chloride (NaCl) | | | | | 7.6 g | 5.84 g |
| Potassium chloride (KCl) | | | | | 0.3 g | 0.23 g |
| sodium bicarbonate (NaHCO3) | | | | | | 2.1 g |
| Sodium phosphate monobasic (NaH2PO4—H2O) | | | | | | 0.04 g |
| (+)-2-hydroxyproprionic acid (Na Lactate) | | | | | | 3.68 ml |
| magnesium chloride (MgCl2) | | | | | 0.1 g | 0.08 g |
| N-(2-hydroxyethyl)piperazine-N'-(2-ethansulfonic acid) (HEPES) | | | | | 2.38 g | 2.38 g |
| tris(hydroxymethyl)amimonethane (TRIS base) | 30.3 g | 32.02 g | 10.28 g | | | |
| Citric Acid Monohydrate | 15.75 g | 18.68 g | | | | |
| Na Citrate Dihydrate | | | | 29 g | | |
| 2-[(2-hydroxy-1,1-bis[hydroxymethyl] ethyl) aminoethanesulfonic acid (TES) | | | 43.25 g | | | |
| Fructose | 12.5 g | 2.67 g | | 10 g | 2.52 g | |
| D-Glucose | | | | 2 g | | |
| Steptamycin | | | | 0.25 g | | |
| Penicillin-G | | | | 0.15 g | | |
| Water | 1 liter | 1 liter | 1 liter | 1 liter | 1 liter | 1 liter |
| target pH | 7.35 | 7.35 | 7.35 | 7.35 | 7.35 | 7.35 |
| target osmolality (milliosmols/kg H2O) | ~314 | ~300 | ~302 | ~316 | ~298 | ~296 | thereby forming a buffered dye solution. Thus, for example, dye in the form of a neat solid, including a free-flowing powder, or a liquid composition may be combined with the buffer, or any constituents of the buffer recipe prior to the combination thereof, to form a buffered dye solution, which may then be combined with neat semen or a sperm suspension.

A variety of biological buffers may be used, individually or in combination, to protect the sperm cells from significant changes in pH and osmotic pressure. Typically, these buffers will be in a concentration of about 0.001M to about 1.0M and at a pH between about 4.5 to about 8.5. Common biological buffers include, for example, phosphates, diphos- The amount of buffer employed generally depends upon several considerations, e.g., the particular buffer and the desired sperm concentration (# sperm/ml) in the staining mixture. Therefore, a sufficient amount of buffer will be used such that the desired concentration of sperm/ml is achieved. In one embodiment, buffer is added to achieve a sperm suspension that contains less than the concentration of sperm in a neat semen sample. In another embodiment, buffer is added to achieve a sperm suspension that contains from about $1 \times 10^6$ sperm/ml to about $5 \times 10^9$ sperm/ml. In another embodiment, buffer is added to achieve a sperm suspension that contains less than about $200 \times 10^6$ sperm/ml. In yet another embodiment, buffer is added to achieve a sperm suspension that contains from about $1 \times 10^6$ sperm/ml to about $200 \times 10^6$ sperm/ml. In still another embodiment, buffer is added to achieve a sperm suspension that contains from about $20 \times 10^6$ sperm/ml to about $200 \times 10^6$ In another embodiment, buffer is added to achieve a sperm suspension that contains from about $30 \times 10^6$ sperm/ml to about $175 \times 10^6$ sperm/ml. In still another embodiment, buffer is added to achieve a sperm suspension that contains from about $50 \times 10^6$ sperm/ml to about $150 \times 10^6$. In yet another embodiment, buffer is added to achieve a sperm suspension that contains from about $100 \times 10^6$ sperm/ml to about $150 \times 10^6$ sperm/ml In still another embodiment, buffer is added to achieve a sperm suspension that contains about $150 \times 10^6$ sperm/ml.

The concentration of the dye in the staining mixture is selected to bind a sufficient amount of dye to the DNA to enable X and Y chromosome-bearing sperm to be sorted into gender enriched populations. In addition, the dye concentration is preferably sufficient to provide quantitative staining of the sperm cells in a reasonably short period without meaningfully impacting cell viability. Factors influencing the desired concentration for a particular application include the nature of the dye, the concentration of sperm in the staining mixture, the pH of the staining mixture, the length of time permitted for uptake of the dye by the sperm cells, and the temperature during this uptake period. In general, however, the concentration of dye in the staining mixture will typically be at any of a range of concentrations, generally between about 0.1 µM and about 1000 µM. For example, the concentration of the dye may be maintained at a "relatively low" concentration range, i.e., a concentration of about 0.1 µM to about 250 µM; within this embodiment, the concentration is preferably from about 100 µM to about 200 µM, more preferably about 100 µM, still more preferably about 200 µM, and even still more preferably about 150 µM. Alternatively, the concentration of the dye may be maintained within an "intermediate" concentration range, i.e., a concentration of about 250 µM to about 700 µM; within this embodiment, the concentration is preferably from about 300 µM to about 700 µM, more preferably about 300 µM, still more preferably about 400 µM, and even still more preferably about 600 µM. In addition, the concentration of the dye may be maintained within a "relatively high" concentration range, i.e., a concentration of about 700 µM to about 1000 µM; within this embodiment, the concentration is preferably from about 800 µM to about 1000 µM, more preferably about 800 µM, still more preferably about 900 µM, and even still more preferably about 1000 µM. Accordingly, in one embodiment, the dye concentration is about 100 µM to about 200 µM. In another embodiment, the dye concentration is about 10 µM to about 100 µM. In another embodiment, the dye concentration is about 20 µM to about 80 µM. In still another embodiment, the dye concentration in the staining mixture is about 20 µM to about 60 µM. In addition, it has been reported that the optimal concentration of stain for most species has been reported to be about 40 µg per $150 \times 10^6$ sperm, which is approximately 70 µM. See, for example, L. A. Johnson and Glenn Welch, *Theriogenology* (1999).

The pH of the staining mixture is preferably maintained in the range of about 6.0 to about 8.0. More preferably, the pH of the staining mixture is maintained in the range of about 7.1 to about 7.6. Still more preferably, the pH of the staining mixture is maintained at about 7.3 to 7.4. Still more preferably, the pH of the staining mixture is maintained at about 7.35.

Certain dyes are capable of permeating the sperm cells and specifically binding the DNA without further intervention to increase the permeability of the cells. With other dyes, however, it may be desirable to treat the sperm prior to staining to increase the rate of permeation without unacceptably reducing viability or motility. Any suitable method known to those skilled in the art may be used. Such methods include electroporation, the use of cell-permeation-enhancing solutions, e.g., mild surfactants, or chemical shock. Where it is desired or advantageous to use other or more stringent techniques, such treatments can include the use of liposomes or many of the techniques which are used by those skilled in the art to introduce stains, dyes, genes, or vectors into living cells. These methods include, but are not limited to microinjection such as used by Gordon et al. (*Proc. Natl. Acad. Sci.*, 1980) and since extended to rabbits, sheep, cattle and pigs; DEAE-dextran-mediated transfer; coprecipitation with calcium phosphate; and other techniques, all of which are well known to one of skill in the art. In yet other instances, it may be desirable to centrifuge the sperm and re-suspend the centrifuged sperm in another medium, albeit based on the same or substantially the same buffer system to remove certain components (which may have previously been added to the sperm suspension) that may interfere with later processing steps.

Uptake of dye by the sperm cells in the staining mixture is allowed to continue for a period of time sufficient to obtain the desired degree of DNA staining. In general, the uptake period will be between about 1 and about 160 minutes. In one embodiment, the uptake period is less than 90 minutes. In another embodiment, the uptake period is less than 60 minutes. In another embodiment, the uptake period is less than 40 minutes. In another embodiment, the uptake period is less than 25 minutes. As previously noted, the uptake period is somewhat dependent upon a range of other parameters, including the uptake temperature, the nature of the dye and the concentration of the dye. In certain embodiments, the uptake period is about 2 to about 25 minutes. In other embodiments, the uptake period is about 5 to 20 minutes. In still other embodiments, the uptake period is about 2 to about 10 minutes. In another embodiment, the uptake period is less than about 2 minutes.

The staining mixture may be subjected to an elevated temperature of the present invention for the entire uptake period or for a fraction thereof. Thus, for example, the staining mixture may be maintained at a temperature in excess of 40° C. for at least 1%, 5%, 10%, 20% or even a greater percentage of the uptake period. In one embodiment, the temperature of the staining mixture is increased during the uptake period. In another embodiment, the temperature of the staining mixture is decreased during the uptake period. In each of these embodiments, however, the rate of temperature change is controlled to preferably avoid any significant negative impact upon sperm cell viability.

In any event, the uptake period is sufficient for the dye to bind to the DNA such that X and Y chromosome-bearing sperm cells can be sorted based upon the differing and measurable fluorescence intensity between the X and Y chromosome-bearing sperm. In one embodiment, the degree of staining is sufficient to permit the X and Y chromosome bearing sperm to be differentially sorted based upon their respective fluorescence into X and Y populations of at least about 60% purity. The degree of staining is preferably sufficient to permit the X and Y chromosome bearing sperm to be differentially sorted based upon their respective fluorescence into X and Y chromosome bearing sperm populations of at least about 70% purity, more preferably at least about 80% purity, even more preferably at least about 85% purity, and still more preferably at least about 90% purity.

Upon being bound to the DNA and excitation with UV or visible light, the dyes of the present invention fluoresce. In one embodiment, the dye is one which fluoresces upon excitation with ultraviolet radiation. Such dyes include, for example, bisbenzimides such as Hoechst 33342 and Hoechst 33258, each of which is commercially available from Sigma-Aldrich (St. Louis, Mo.). Advantageously, for example, Hoechst 33342 has a low toxicity, is sufficiently cell permeable, is specific for DNA, has a fluorescence that is dramatically enhanced after binding to DNA, and displays a linear relationship between the intensity of the fluorescence and the amount of DNA present in a given cell or sample.

In another embodiment, the dye is one which fluoresces upon excitation with visible light. Such dyes include, for example, the visible light excitable dye, SYBR-14, commercially available from Molecular Probes, Inc. (Eugene, Oreg.) and the bisbenzimide-BODIPY® conjugate 6-{[3-((2Z)-2-{[1-(difluoroboryl)-3,5-dimethyl-1H-pyrrol-2-yl]methylene}-2H-pyrrol-5-yl)propanoy]amino}-N-(methyl{3-[({4-[6-(4-methylpiperazin-1-yl)-1H,3'H-2,5'-bibeenzimdazol-2'-yl]phenoxy}acetyl)amino]propyl}amino)propyl]hexanamide ("BBC")described in WO 02/41906.

In one embodiment of the present invention, the dye may be modified by conjugation to another moiety. For example, in accordance with a particular aspect of the invention, the bisbenzimide (bisbenzimidazole) can be modified by addition of a fluorophore that results in a fluorescence response by the conjugate to excitation by visible light. Preferably these conjugate molecules resemble the bisbenzimide molecule in that binding to DNA enhances their fluorescence, and represent an improvement over the bisbenzimide molecule in that the conjugates fluoresce in response to visible light Particularly preferred fluorophores are visible-light-excitable dipyrromethenboron difluoride derivatives. Dipyrromethenboron difluoride dyes are membrane permeant fluorescent compounds available from Molecular Probes Inc. under the BODIPYO trademark as described in, for example, U.S. Pat. Nos. 5,338,854 and 4,774,339, herein incorporated by reference. Preparation of an exemplary bisbenzimide-dipyrromethenboron difluoride conjugate is described WO 02/41906. Other fluorophores of the class described in the preceding paragraph, such as, for example, fluoroscein and its derivatives may also be used.

Those skilled in the art will appreciate that such fluorophore-modified dyes, may be prepared by modifying or functionalizing the conjugate DNA stains with otherwise suitable properties so that they have sufficient cell permeability in the desired pH and temperature ranges. For example, chemical modifications can be made to enhance appropriate cell permeability by (1) changing the pKa of the DNA dye, (2) adding an ionic permeability-enhancing group, either cationic or anionic, attached through an appropriate linker, or (3) adding nonionic permeability-enhancing groups such as ethylene glycol or polyethylene glycol moieties.

Within the scope of the invention, the bisbenzimide and visible wavelength fluorophore can be connected in many different ways. WO 02/41906 illustrates one way they can be connected; however, persons skilled in the art can readily select many other fluorophores and methods of connection. Supplies and consultation services to assist in such selection are readily available to those skilled in the art from commercial entities in the business of making and selling the fluorophores such as, for example, Molecular Probes Inc., (Eugene, Oreg.).

Preferably, the chemical entity linking the bisbenzimide to the visible wavelength fluorophore will be selected to not result in significant negative effects upon viability, permeability, stability, uptake, cell storage, flow cytometry, formulation, or fluorescence properties. Preferably the chemical functionality of the linking entity will be selected to enhance properties such as stability, permeability, viability, uptake, cell storage, flow cytometry, formulation, or fluorescence properties.

The methods disclosed herein may be applied either to sperm recently obtained from the particular source (i.e., obtained from bovine, porcine, or other mammalian source within minutes or hours before staining) or to sperm that have been cryopreserved and subsequently thawed. In either instance, the results of the cytometric sorting may be improved by the addition of a quencher to the staining solution to reduce the fluorescence of dead sperm. Various quenchers, as well as the use of the same, are well known in the art, as is demonstrated with respect to propidium iodide (Garner et al., *Bio. of Reprod.*, 53: 276-84 (1995)) and FD&C #40 (Johnson et al., *Theriogenology*, 52: 1323-1341 (1999)). FD&C #40 is especially useful in this method, as it is nontoxic if used in low concentrations. Likewise, the combination of SYBR-14 and propidium iodide is advantageous, as this allows visualization and separation of live sperm cells from moribund and dead cells. Accordingly, in one embodiment of the invention, the sperm cells are combined with both a dye and a quencher to form a staining mixture. In a preferred embodiment, the sperm cells are combined with Hoechst 33342 and FD&C #40. In yet another embodiment, the sperm cells are combined with SYBR-14 and propidium iodide. While quenchers are useful when sorting thawed cryopreserved sperm samples, it is to be understood that their use is not solely limited to such, and that they may be used advantageously on samples of recently obtained sperm.

In addition to buffer, other additives may be included in the staining mixture to enhance the viability or motility of the sperm; these additives may be provided as part of the sperm source, the dye source, or separately to the staining mixture. Such additives include energy sources, antibiotics, compositions which regulate oxidation/reduction reactions intracellularly or extracellularly, motility inhibitors, and seminal plasma.

In general, motility inhibitors cause the cells in the staining mixture to emulate sperm cells of the epididymis of a mammal, such as for example a bull, by simulating the fluid environment of the epididymis or epididymal tract of the mammal; thus for example, the inhibitor(s) inhibit the metabolic activity and/or the motility of the sperm. The inhibitor may be any of a range of compositions having a depressive effect upon sperm motility. For example, relatively high concentrations of potassium ions in the staining mixture tend to depress sperm motility. In one embodiment, therefore, it is preferred that the staining mixture contain a source of potassium ions and that the potassium concentration in the staining mixture be at least about 0.05 moles/L. More preferably, the potassium concentration is at least about 0.05 moles/L to about 0.5 moles/L. Still more preferably, the potassium concentration is at least about 0.1 moles/L to about 0.3 moles/L. Most preferably, the potassium concentration is at about 0.173 moles/L. Such staining mixtures will typically, but not necessarily, also contain a source of sodium ions. When sodium is present, the molar ratio of potassium to sodium is greater than 1:1, respectively. Preferably, the molar ratio of potassium to sodium is at least about 1.25:1. Still more preferably, the molar ratio of potassium to sodium is at least about 1.5:1. Still more preferably, the molar ratio of potassium to sodium is at least about 1.75:1. Still more preferably, the molar ratio of potassium to sodium is at least about 1.78:1. In one particular embodiment, the molar ration of potassium to sodium is at least about 2:1.

The staining mixture may additionally comprise an ion or source of carbon dioxide capable of down-regulating uptake of carbohydrate. In this embodiment, the source of carbon dioxide may be, for example, one or more carbonates. In one embodiment, the staining mixture comprises $NaHCO_3$ and $KHCO_3$, thereby providing a source potassium and sodium ions as well as a partial pressure of carbon dioxide. For example, in one embodiment, the staining mixture comprises $NaHCO_3$ and $KHCO_3$ in an aqueous solution, preferably $NaHCO_3$, $KHCO_3$, and $C_6H_8O_7 \cdot H_2O$ in water; by way of further example, the staining mixture may be formed using an inhibitory buffer comprising 0.097 moles/L of $NaHCO_3$, 0.173 moles/L of $KHCO_3$, 0.090 moles/L $C_6H_8O_7 \cdot H_2O$ in water as disclosed in Salisbury & Graves, *J. Reprod. Fertil.*, 6:351-359 (1963). The sperm cells will generally remain quiescent as long as they are exposed to the motility inhibitor(s).

Examples of such a composition which regulates oxidation/reduction reactions intracellularly or extracellularly include, for example, pyruvate, vitamin K, lipoic acid, glutathione, flavins, quinones, superoxide dismutase (SOD), and SOD mimics. If included in the staining mixture, such a composition may be present in a concentration sufficient to effect the protective effect without detrimentally affecting sperm health. Exemplary concentration ranges include from about 10 μM to about 50 mM depending upon such factors as the particular composition being used or the concentration of sperm in the staining mixture. For example, if pyruvate is included in the composition, it may be present in the staining mixture in a concentration from about 0.5 μM to about 50 mM, preferably from about 1 mM to about 40 mM, more preferably from about 2.5 mM to about 25 mM, still more preferably from about 10 mM to about 20 mM, even still more preferably at about 15 mM, and most preferably at about 10 mM. If vitamin K is included in the composition, it may be present in the staining mixture in a concentration from about 1 μM to about 100 μM, preferably from about 10 μM to about 100 μM, more preferably from about 50 μM to about 100 μM, and most preferably at about 100 μM. If lipoic acid is included in the composition, it may be present in the staining mixture in a concentration from about 0.1 mM to about 1 mM, preferably from about 0.5 mM to about 1 mM, more preferably about 0.5 mM, and most preferably about 1 mM. The staining mixture may comprise any one of the above listed embodiments of the composition or any combination thereof in the above listed concentrations. For example, the staining mixture may comprise a composition which regulates oxidation/reduction reactions intracellularly or extracellularly comprising pyruvate in a concentration of about 10 mM and vitamin K in a concentration of about 100 μM. Alternatively, the staining mixture may comprise a composition comprising pyruvate in a concentration of about 10 mM and lipoic acid in a concentration of about 1 mM. Yet another example includes a staining mixture comprising a composition comprising pyruvate in a concentration of about 10 mM, vitamin K in a concentration of about 100 μM, and lipoic acid in a concentration of about 1 mM.

Once the sperm are stained according to the present invention, they may be prepared for sorting and then sorted according to any known means that allows for separation based upon fluorescence. Commonly used and well known methods include flow cytometry systems, as exemplified by and described in U.S. Pat. Nos. 5,135,759, 5,985,216, 6,071,689, 6,149,867, and 6,263,745, as well as WO 99/33956 and WO 01/37655. In one embodiment, for example, the stained cells may be combined with a sheath fluid or otherwise prepared for sorting while being maintained at an elevated temperature of the present invention. In another embodiment, for example, the stained cells are cooled from the elevated temperature at which dye uptake occurs to a lesser temperature, e.g., room temperature, at which later processing steps are to be carried out; to enable the desired degree of separation in this embodiment, however, it is generally preferred that no significant amount of dye uptake occurs at temperatures less than the elevated temperatures of the present invention.

EXAMPLES

Example 1

Bull semen was collected from a sexually mature bull using an artificial vagina and the sample transported at 37° C. in a temperature-controlled container to the staining facility. Upon receipt, the semen was analyzed for concentration, visual motility, pH, and membrane integrity, motility and progressive motility by the Hamilton-Thorn Motility Analyzer (IVOS), according to a standard and well known procedures (Farrell et al. *Theriogenology*, 49(4): 871-9 (March 1998)). Based on the semen concentration, 8×5 mL sperm suspensions were prepared. Four samples of 5 mL of $150 \times 10^6$ sperm/mL were prepared by suspending an aliquot of semen in 41° C. TCA buffer pH 7.35. Four additional samples of 5 mL of $150 \times 10^6$ sperm/mL were prepared by suspending an aliquot of semen in 39° C. TCA buffer at pH 7.35. To the sperm suspensions, aliquots of a 10 mM Hoechst solution in water were added to yield the dye concentrations as seen in Table 1 ("Target Concentration of Hoechst (μM)"). The sperm suspensions were maintained in 41° C. and 39° C. water baths. Sperm suspensions were analyzed by removing an aliquot of 500 μL from sperm suspension samples and analyzing by flow cytometry to measure the uptake of the dye (i.e., to determine the Fluorescence Intensity).

TABLE 1

| Tube # | Temperature (° C.) | Target concentration of Hoechst (μM) | μL 10 mM Hoechst 33342 to be added to 5 mL of sperm suspension |
|---|---|---|---|
| 1 | 39° C. | 20 μM | 10 μL |
| 2 | 41° C. | 20 μM | 10 μL |
| 3 | 39° C. | 30 μM | 15 μL |
| 4 | 41° C. | 30 μM | 15 μL |
| 5 | 39° C. | 57 μM | 28.5 μL |
| 6 | 41° C. | 57 μM | 28.5 μL |
| 7 | 39° C. | 85 μM | 42.5 μL |
| 8 | 41° C. | 85 μM | 42.5 μL |

Results of the analysis are summarized in FIGS. 1A-1D.

Example 2

Sperm samples were obtained and prepared in the same manner as in Example 1 with the exception of the dye concentrations of Hoechst 33342 used to stain the sperm. Table 2 lists the concentrations used in Example 2. The suspensions were maintained in 41° C. and 39° C. water baths. Sample aliquots of 500 µL were removed periodically from each sample and analyzed by flow cytometry to determine the Fluorescence Intensity.

TABLE 2

| Tube # | Temperature (° C.) | Target concentration of Hoechst (µM) | µL 10 mM Hoechst 33342 to be added to 5 mL of sperm suspension |
|---|---|---|---|
| 1 | 39° C. | 20 µM | 10 µL |
| 2 | 41° C. | 20 µM | 10 µL |
| 3 | 39° C. | 30 µM | 15 µL |
| 4 | 41° C. | 30 µM | 15 µL |
| 5 | 39° C. | 40 µM | 20 µL |
| 6 | 41° C. | 40 µM | 20 µL |
| 7 | 39° C. | 60 µM | 30 µL |
| 8 | 41° C. | 60 µM | 30 µL |

Results of the analysis are summarized in FIGS. 2A-2D.

Example 3

Sperm samples were obtained, prepared, stained, and analyzed in the same manner as in Example 1 with the exception of the dye concentrations of Hoechst 33342 used to stain the sperm and the staining temperatures. Table 3 lists the concentrations and temperatures used in Example 3.

TABLE 3

| Tube # | Temperature (° C.) | Target concentration of Hoechst (µM) | µL 10 mM Hoechst 33342 to be added to 5 mL of sperm suspension |
|---|---|---|---|
| 1 | 39° C. | 60 µM | 30 µL |
| 2 | 43° C. | 60 µM | 30 µL |
| 3 | 39° C. | 40 µM | 20 µL |
| 4 | 43° C. | 40 µM | 20 µL |
| 5 | 39° C. | 30 µM | 15 µL |
| 6 | 43° C. | 30 µM | 15 µL |
| 7 | 39° C. | 20 µM | 10 µL |
| 8 | 43° C. | 20 µM | 10 µL |

Results of the analysis are summarized in FIGS. 3A-3D.

Example 4

Sperm samples were obtained, prepared, stained, and analyzed in the same manner as in Example 1 with the exception of the dye concentrations of Hoechst 33342 used to stain the sperm and the staining temperatures. Table 4 lists the concentrations and temperatures used in Example 4.

TABLE 4

| Tube # | Temperature (° C.) | Target concentration of Hoechst (µM) | µL 10 mM Hoechst 33342 to be added to 5 mL of sperm suspension |
|---|---|---|---|
| 1 | 39° C. | 80 µM | 40 µL |
| 2 | 43° C. | 80 µM | 40 µL |
| 3 | 39° C. | 100 µM | 50 µL |
| 4 | 43° C. | 100 µM | 50 µL |

Figure 4A:
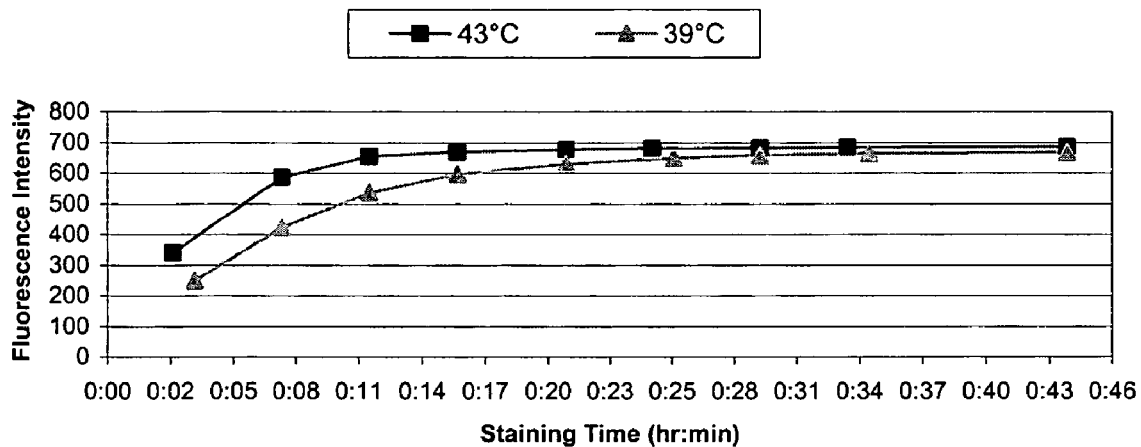
FIGS. 4A and 4B graphically depict the results of the study carried out in Example 4 wherein fluorescence intensity of sperm is measured for sperm stained at varying concentrations of Hoechst 33342 dye at 39° C. and 43° C.
Figure 4B:
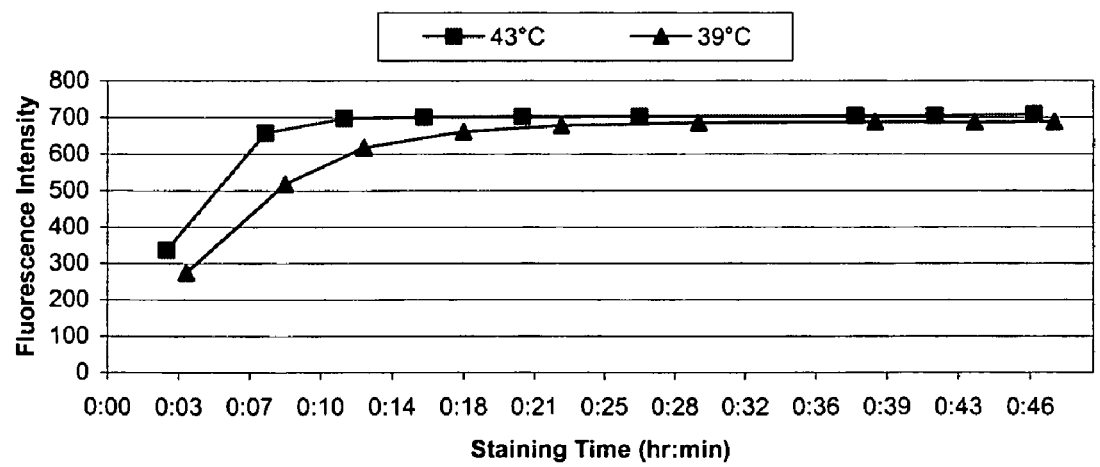

Results of the analysis are summarized in FIGS. 4A and 4B.

Example 5

Sperm samples were obtained, prepared, stained, and analyzed in the same manner as in Example 1 with the exception of the dye concentrations of Hoechst 33342 used to stain the sperm and the staining temperatures. Table 5 lists the concentrations and temperatures used in Example 5.

TABLE 5

| Tube # | Temperature (° C.) | Target concentration of Hoechst (µM) | µL 10 mM Hoechst 33342 to be added to 5 mL of sperm suspension |
|---|---|---|---|
| 5 | 39° C. | 80 µM | 40 µL |
| 6 | 45° C. | 80 µM | 40 µL |
| 7 | 39° C. | 100 µM | 50 µL |
| 8 | 45° C. | 100 µM | 50 µL |

Figure 5A:
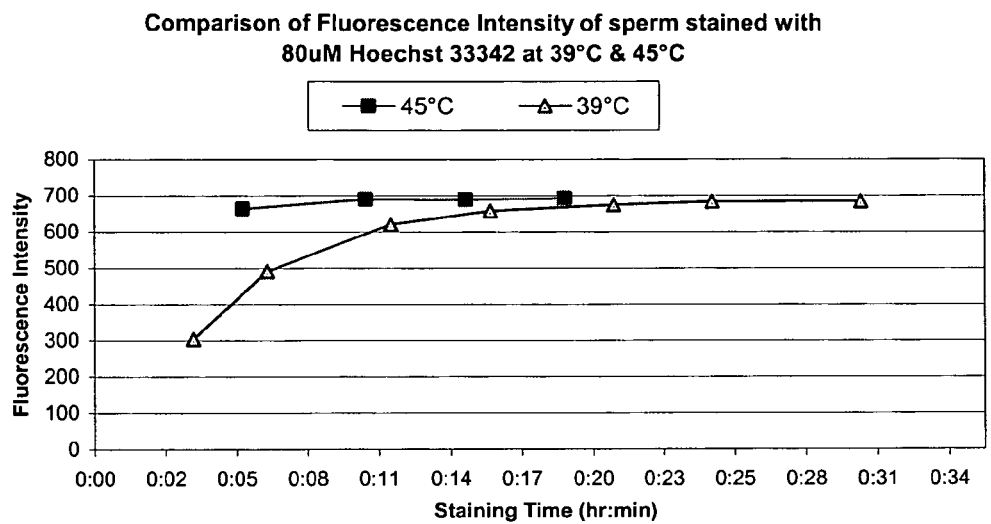
FIGS. 5A and 5B graphically depict the results of the study carried out in Example 5 wherein fluorescence intensity of sperm is measured for sperm stained at varying concentrations of Hoechst 33342 dye at 39° C. and 45° C.
Figure 5B:
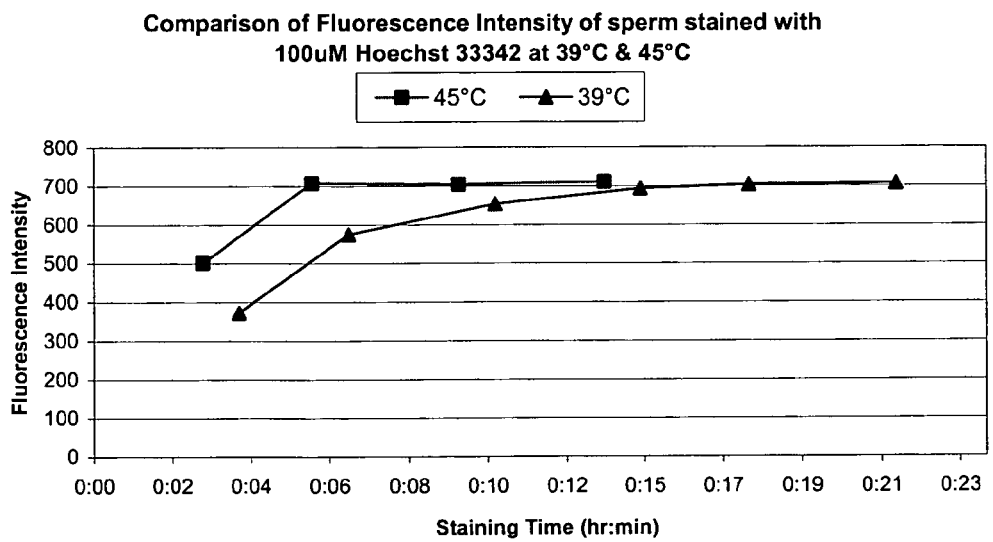

Results of the analysis are summarized in FIGS. 5A and 5B.

Example 6

Sperm samples were obtained, prepared, stained, and analyzed in the same manner as in Example 1 with the exception of the dye concentrations of Hoechst 33342 used to stain the sperm and the staining temperatures. Table 6 lists the concentrations and temperatures used in Example 6.

TABLE 6

| Tube # | Temperature (° C.) | Target concentration of Hoechst (µM) | µL 10 mM Hoechst 33342 to be added to 5 mL of sperm suspension |
|---|---|---|---|
| 1 | 39° C. | 60 µM | 30 µL |
| 2 | 47° C. | 60 µM | 30 µL |
| 3 | 39° C. | 150 µM | 75 µL |
| 4 | 43° C. | 150 µM | 75 µL |

Figure 6A:
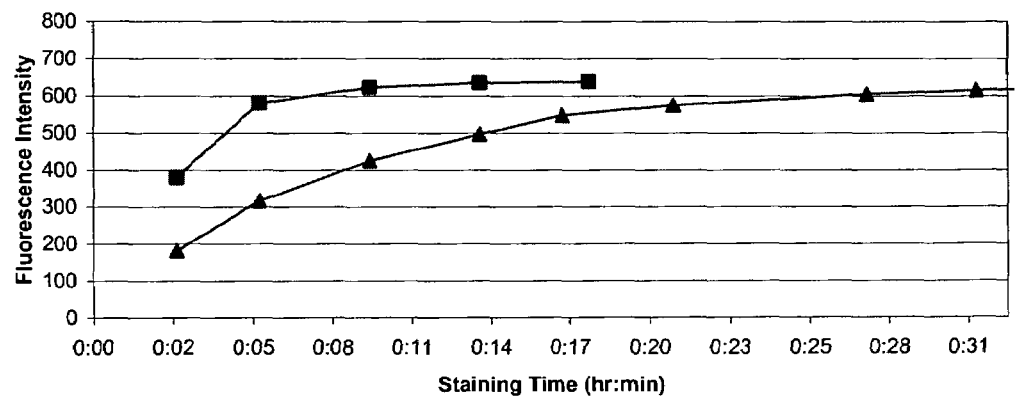
FIGS. 6A and 6B graphically depict the results of the study carried out in Example 6 wherein fluorescence intensity of sperm is measured for sperm stained at varying concentrations of Hoechst 33342 dye at 39° C. and 47° C.
Figure 6B:
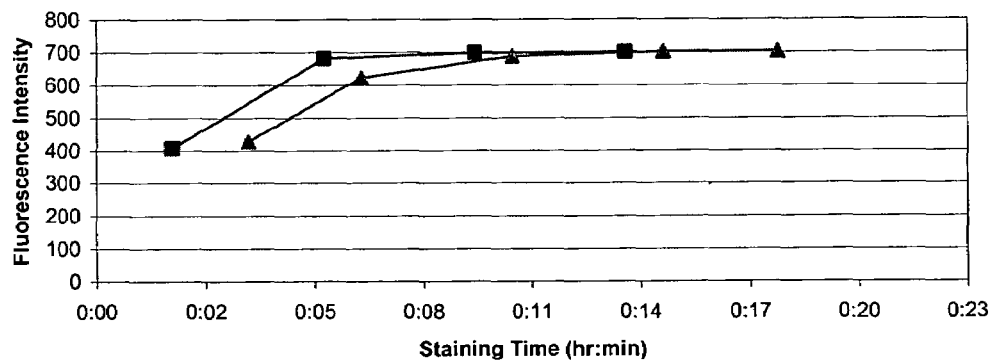

Results of the analysis are summarized in FIGS. 6A and 6B.

Example 7

Figure 7A:
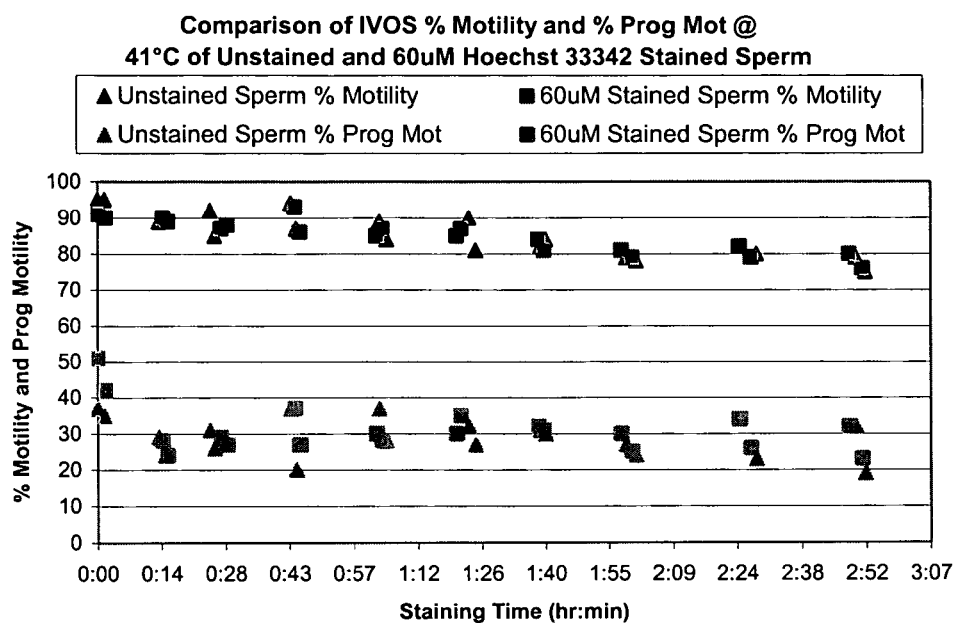
FIGS. 7A and 7B graphically depict the results of the study carried cut in Example 7 wherein percent motility and percent progressive motility of sperm are measured for sperm unstained or stained with 60 μM Hoechst 33342 dye at 39° C. 41° C. and 43° C.
Figure 7B:
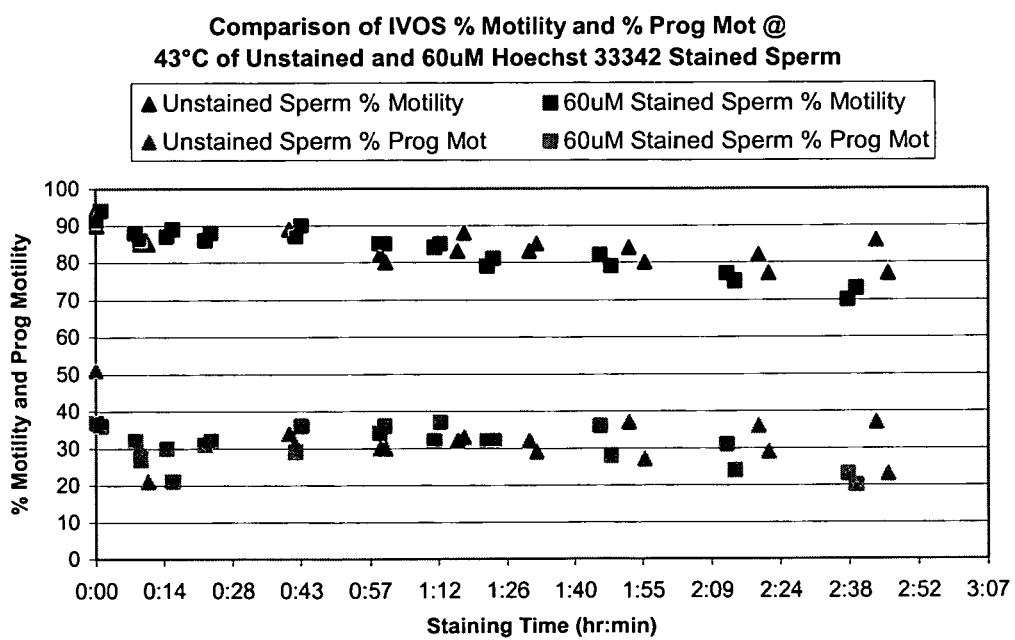

Bull semen was collected from a sexually mature bull using an artificial vagina and the sample transported at 25° C. in a temperature-controlled container to the staining facility. Upon receipt, the semen was analyzed for concentration, visual motility, IVOS motility and progressive motility, pH, and membrane integrity by known analytical methods. Based on the semen concentration, 4×1 mL of $150 \times 10^6$ sperm/mL sperm suspensions were prepared. Two samples of 1 mL of $150 \times 10^6$ sperm/mL were prepared by suspending an aliquot of semen in 41° C. TCA buffer at pH 7.35. Two additional samples of 1 mL of $150 \times 10^6$ sperm/mL were prepared by suspending an aliquot of semen in 43° C. TCA buffer at pH 7.35. To one sample of each temperature was added 6 µL of 10 mM Hoechst solution to yield the dye concentration of 60 µM. The suspensions were maintained in 41° C. and 43° C. water baths. Periodically 50 µL aliquots were removed from the sperm suspension samples, transferred to a conical tube and 200 µL of the appropriate temperature TCA buffer added, to yield a final sperm suspension concentration of 30×10⁶ sperm/mL. The 30×10⁶ sperm/mL sperm suspension samples were immediately analyzed by IVOS. IVOS results for % Motility and % Progressive Motility (Prog Mot) are shown in FIGS. 7A and 7B.

Example 8

Figure 8A:
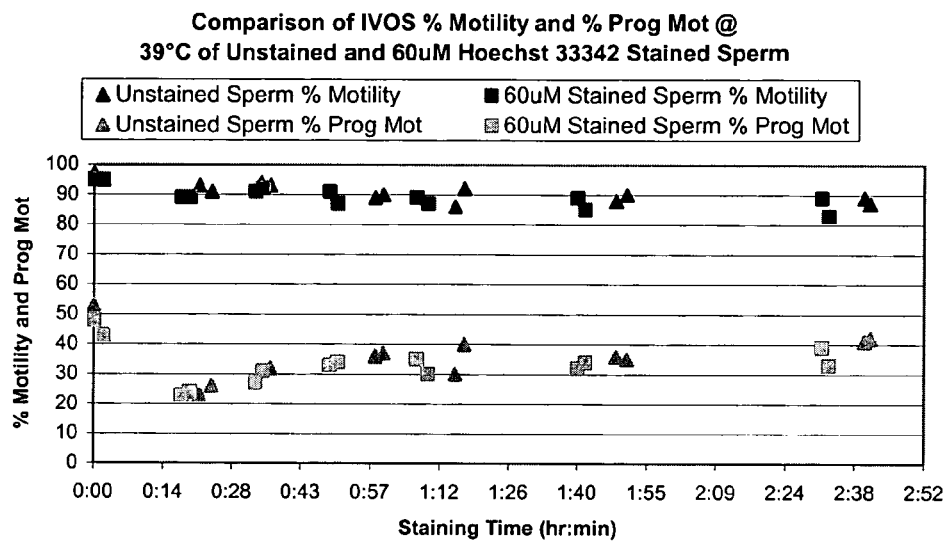
FIGS. 8A and 8B graphically depict the results of the study carried out in Example 8 wherein percent motility and percent progressive motility of sperm are measured for sperm unstained or stained with 60 μM Hoechst 33342 dye at 39° C. and 45° C.
Figure 8B:
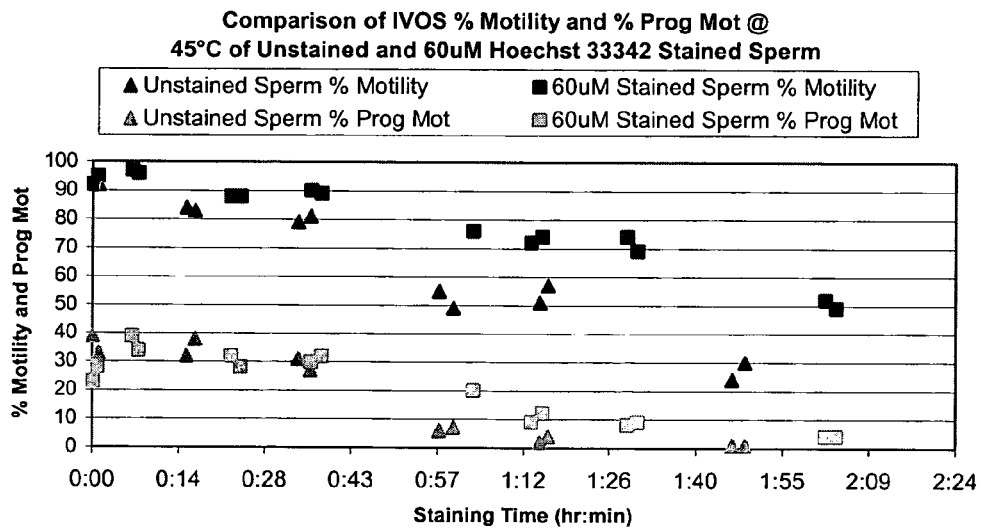

Bull semen was collected, analyzed, suspended in buffer, stained with Hoechst 33342, and analyzed by IVOS as in Example 7 with the following exception. Samples were stained at a concentration of 60 μM and maintained at a temperature of 39° C. and 45° C. Results of the IVOS analysis are shown in FIGS. 8A and 8B.

Example 9

Figure 9A:
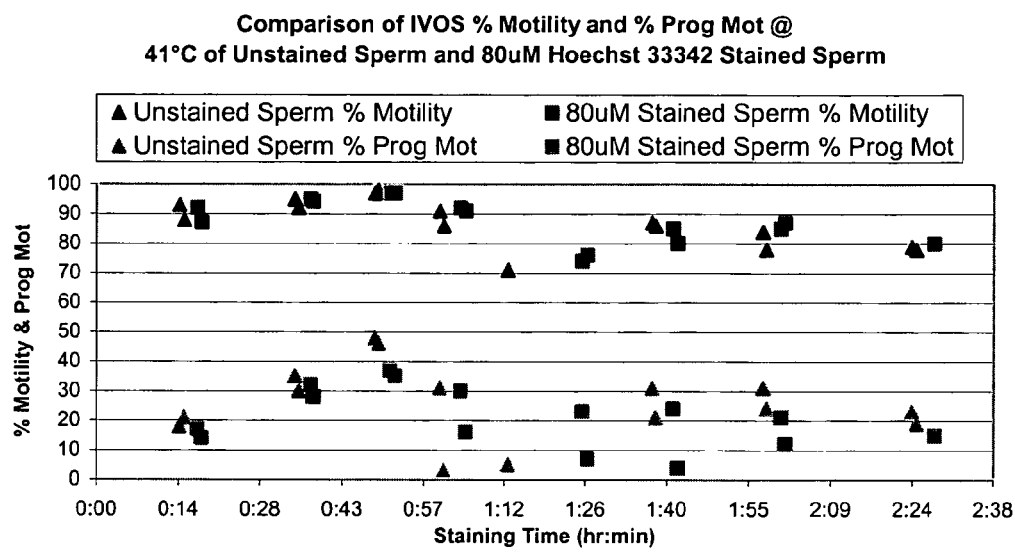
FIGS. 9A-9C graphically depict the results of the study carried out in Example 9 wherein percent motility and percent progressive motility of sperm are measured for sperm unstained or stained with 80 μM Hoechst 33342 dye at 41° C., 43° C., and 45° C.
Figure 9B:
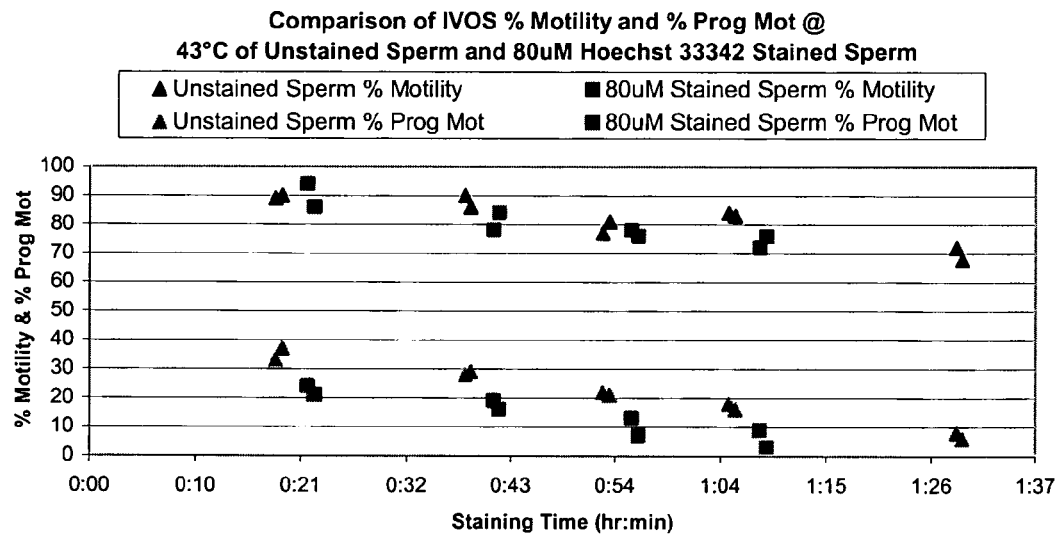
Figure 9C:
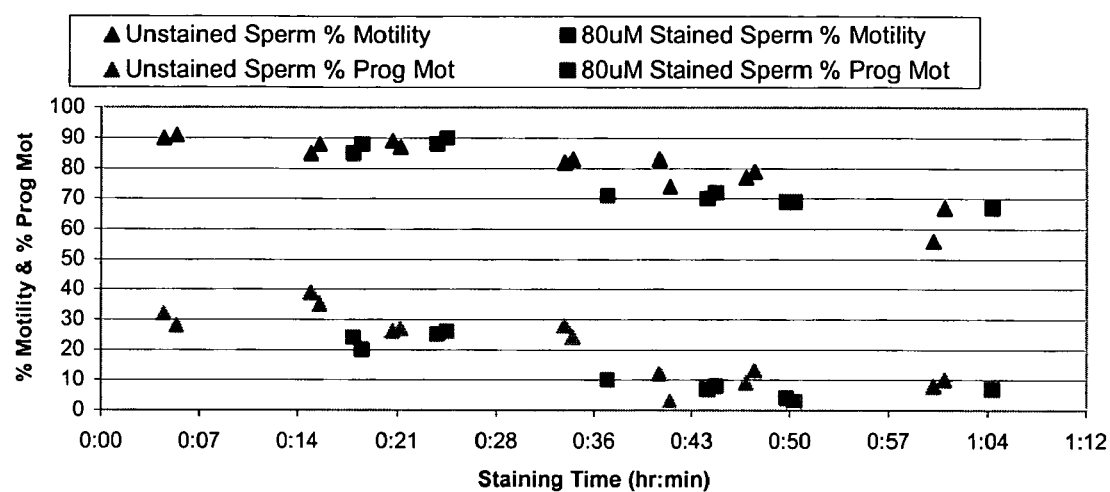

Bull semen was collected, analyzed, suspended in buffer, stained with Hoechst 33342, and analyzed by IVOS as in Example 7 with the following exception. Samples were stained at a concentration of 80 μM and maintained at temperatures of 41° C., 43° C., and 45° C. Results of the IVOS analysis are shown in FIGS. 9A-9C.

Example 10

Figure 10A:
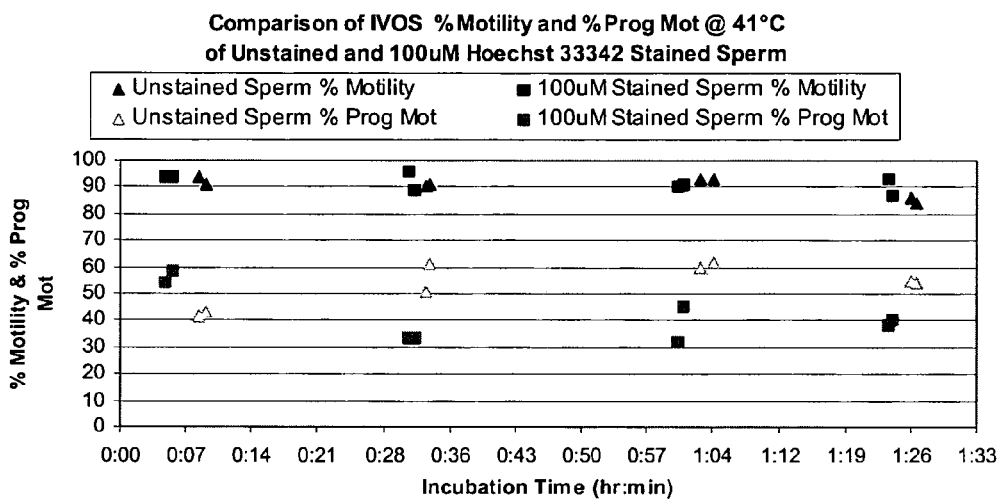
FIGS. 10A-10C graphically depict the results of the study carried out in Example 10 wherein percent motility and percent progressive motility of sperm are measured for sperm unstained or stained with 100 μM Hoechst 33342 dye at 41° C., 43° C., and 45° C.
Figure 10B:
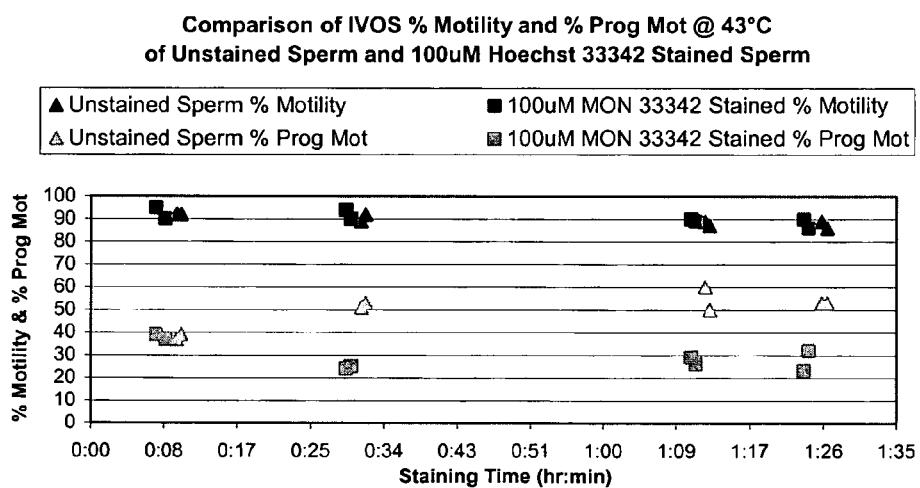
Figure 10C:
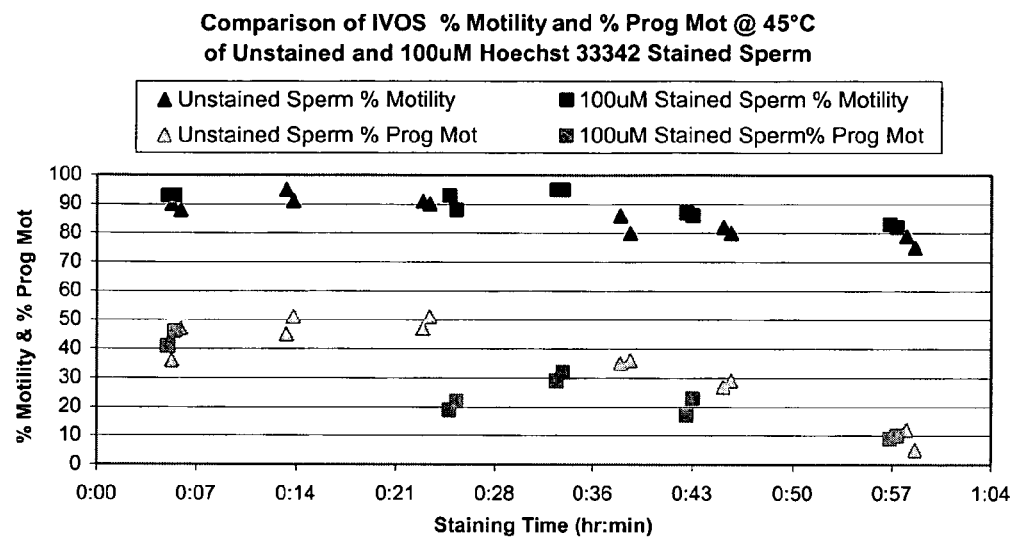

Bull semen was collected, analyzed, suspended in buffer, stained with Hoechst 33342, and analyzed by IVOS as in Example 7 with the following exception. Samples were stained at a concentration of 100 μM and maintained at temperatures of 41° C., 43° C., and 45° C. Results of the IVOS analysis are shown in FIGS. 10A-10C.

Example 11

Figure 11:
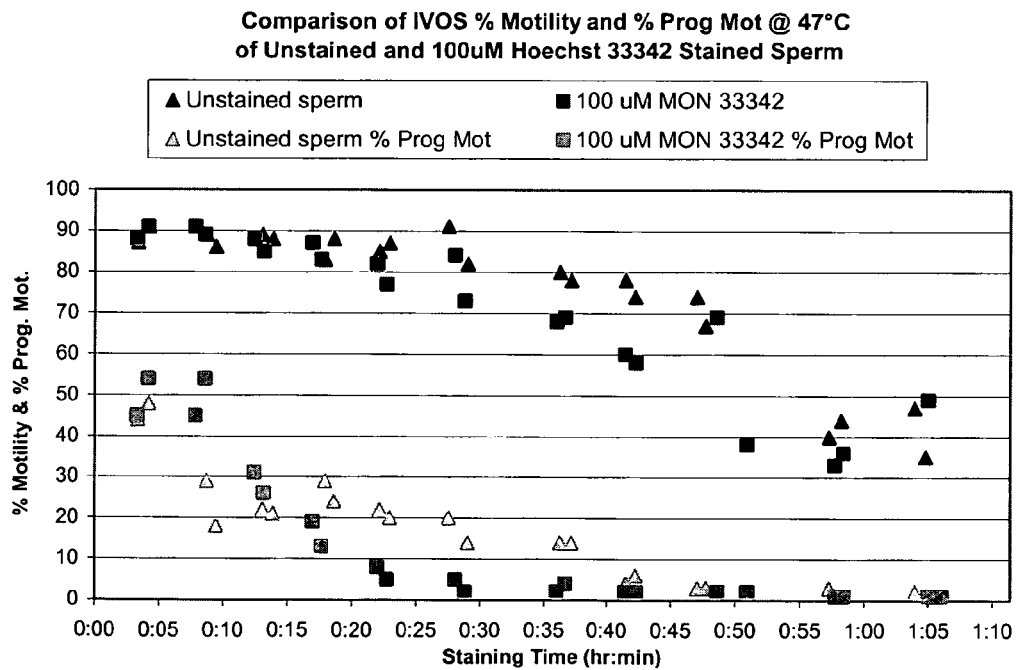
FIG. 11 graphically depicts the results of the study carried out in Example 11 wherein percent motility and percent progressive motility of sperm are measured for sperm unstained or stained with 100 μM Hoechst 33342 dye at 47° C.

Bull semen was collected, analyzed, suspended in buffer, stained with Hoechst 33342, and analyzed by IVOS as in Example 7 with the following exception. Samples were stained at a concentration of 100 μM and maintained at a temperature of 47° C. Results of the IVOS analysis are shown in FIG. 11.

Example 12

Figure 12:
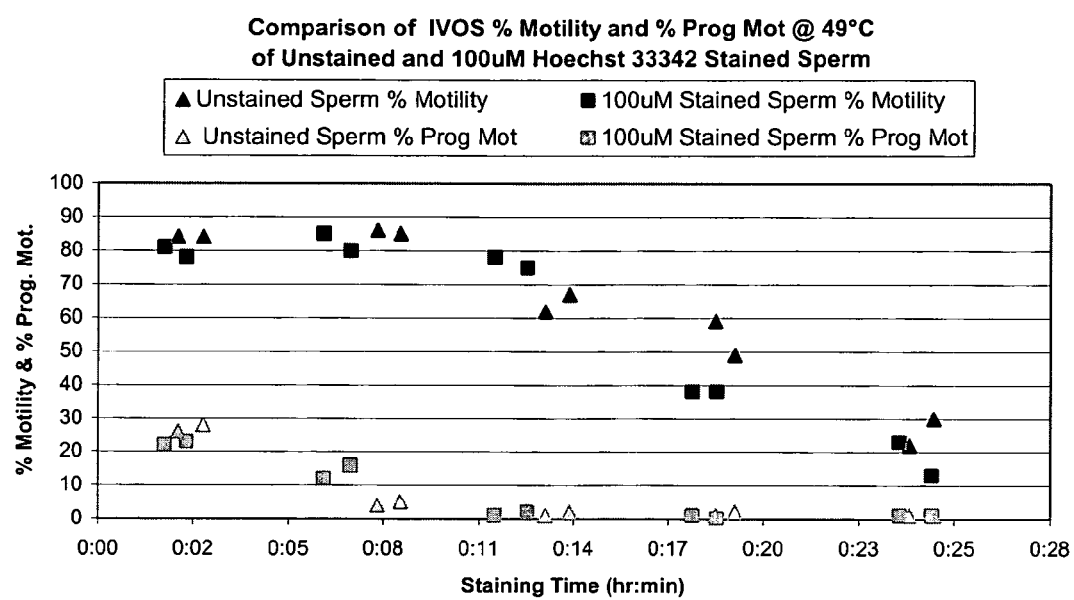
FIG. 12 graphically depicts the results of the study carried out in Example 12 wherein percent motility and percent progressive motility of sperm are measured for sperm unstained or stained with 100 μM Hoechst 33342 dye at 49° C.

Bull semen was collected, analyzed, suspended in buffer, stained with Hoechst 33342, and analyzed by IVOS as in Example 7 with the following exception. Samples were stained at a concentration of 100 μM and maintained at a temperature of 49° C. Results of the IVOS analysis are shown in FIG. 12.

Example 13

Figure 13A:
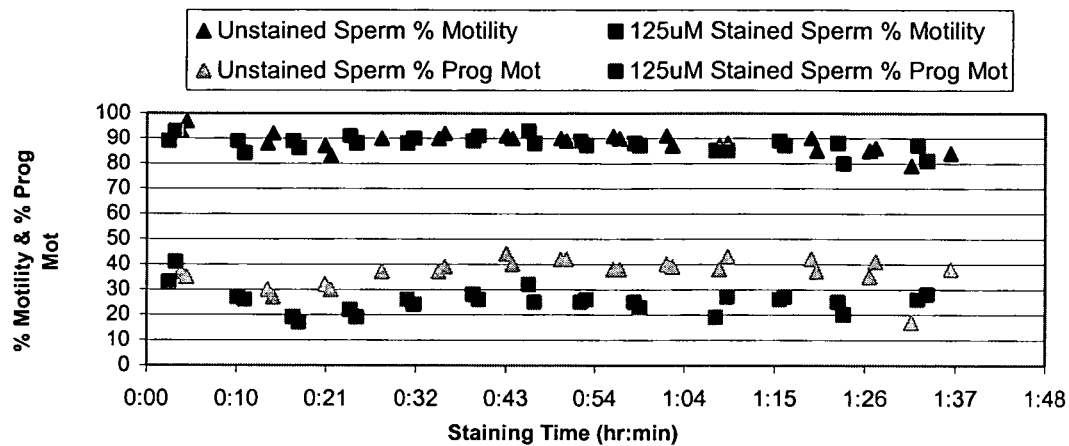
FIGS. 13A and 13B graphically depict the results of the study carried out in Example 13 wherein percent motility and percent progressive motility of sperm are measured for sperm unstained, stained with 125 μM Hoechst 33342 dye, or stained with 150 μM Hoechst 33342 dye at 43° C.
Figure 13B:
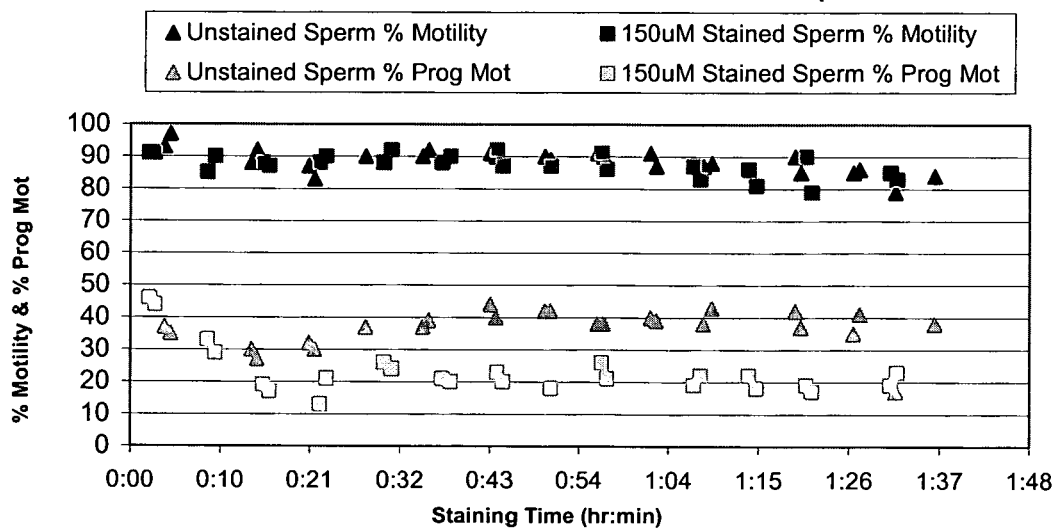

Bull semen was collected, analyzed, suspended in buffer, stained with Hoechst 33342, and analyzed by IVOS as in Example 7 with the following exception. Samples were stained at a concentration of 125 μM and 150 μM, and each was maintained at a temperature of 43° C. in a water bath. Results of the IVOS analysis are shown in FIGS. 13A and 13B.

Example 14

Figure 14A:
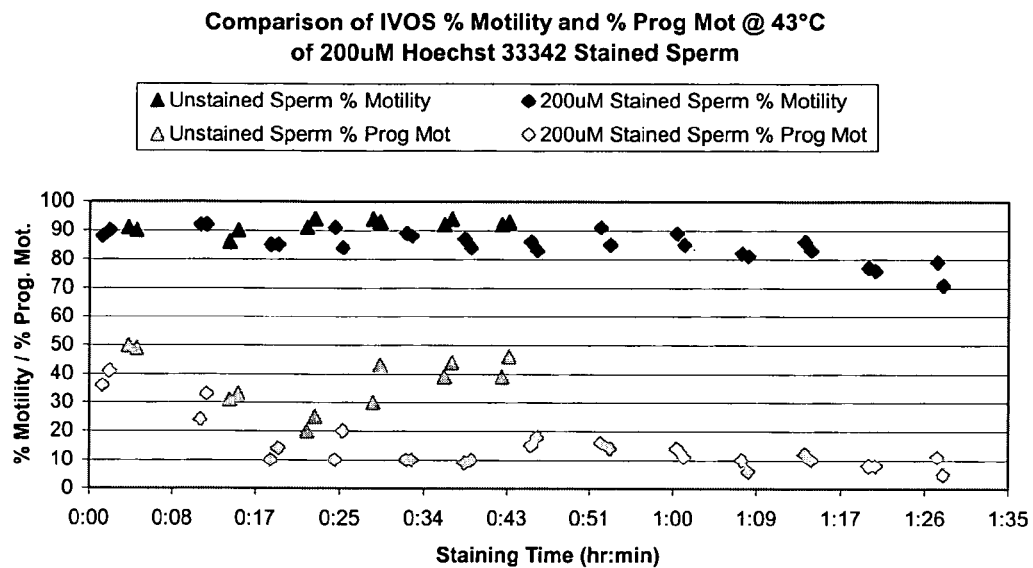
FIGS. 14A and 14B graphically depict the results of the study carried out in Example 14 wherein percent motility and percent progressive motility of sperm are measured for sperm unstained, stained with 200 μM Hoechst 33342 dye, or stained with 250 μM Hoechst 33342 dye at 43° C.
Figure 14B:
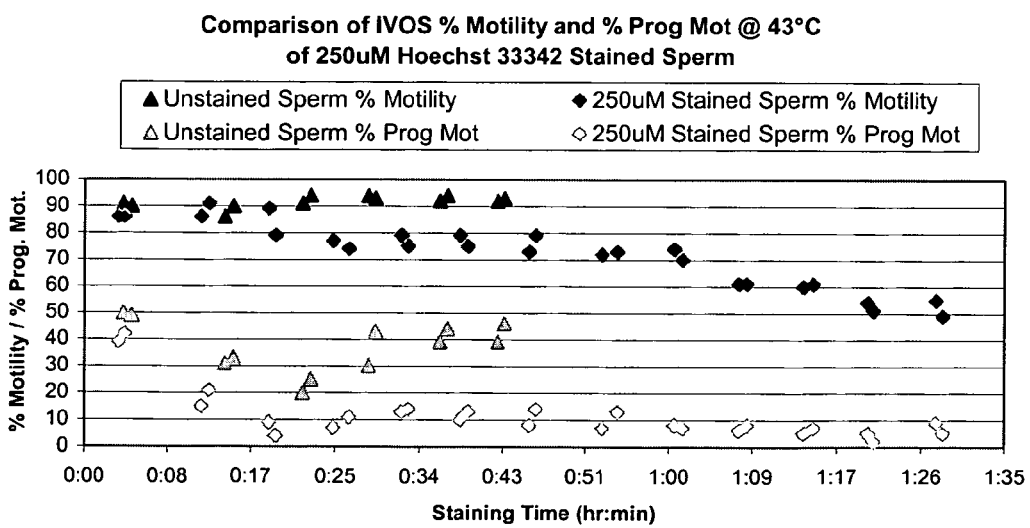

Bull semen was collected, analyzed, suspended in buffer, stained with Hoechst 33342, and analyzed by IVOS as in Example 7 with the following exception. Samples were stained at a concentration of 200 μM and 250 μM, and each was maintained at a temperature of 43° C. in a water bath. Results of the IVOS analysis are shown in FIGS. 14A and 14B.

Example 15

Figure 15A:
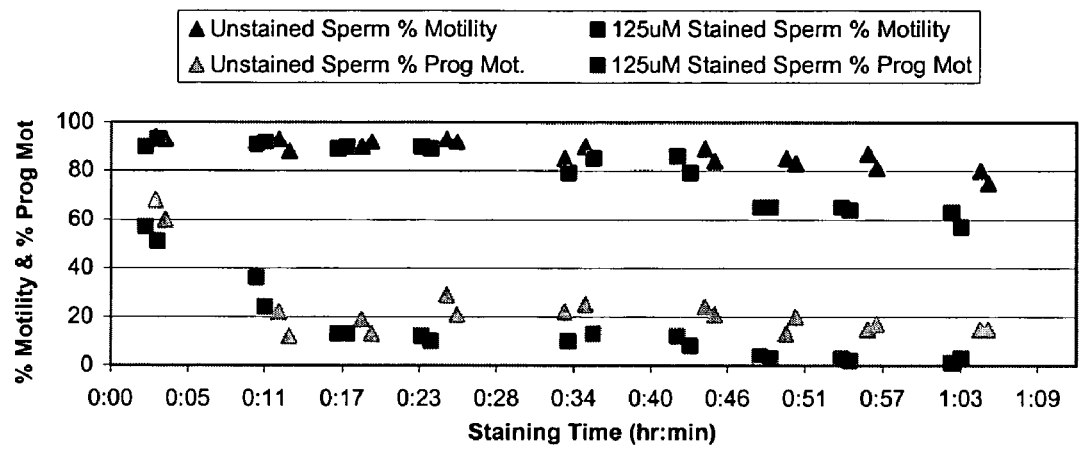
FIGS. 15A and 15B graphically depict the results of the study carried out in Example 15 wherein percent motility and percent progressive motility of sperm are measured for sperm unstained, stained with 125 μM Hoechst 33342 dye, or stained with 150 μM Hoechst 33342 dye at 45° C.
Figure 15B:
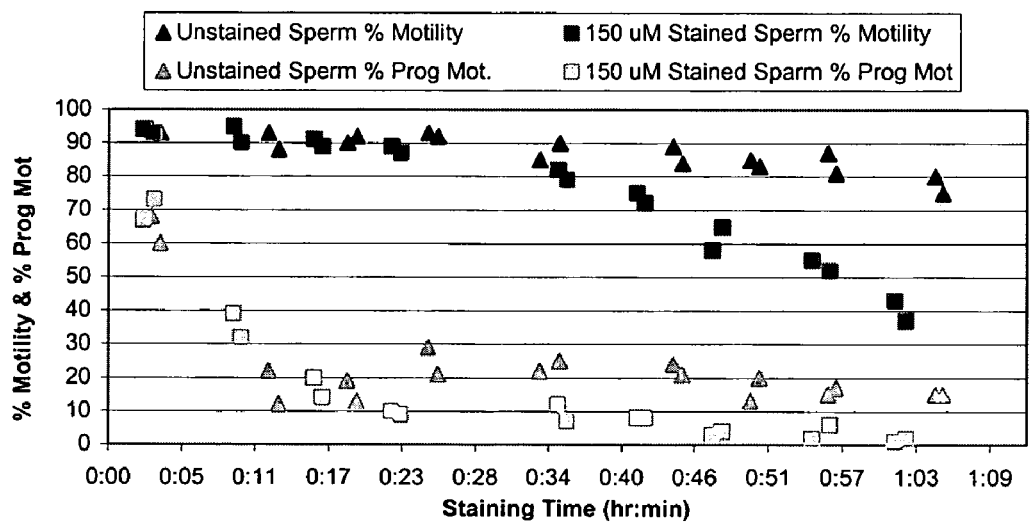

Bull semen was collected, analyzed, suspended in buffer, stained with Hoechst 33342, and analyzed by IVOS as in Example 7 with the following exception. Samples were stained at a concentration of 125 μM and 150 μM, and each was maintained at a temperature of 45° C. in a water bath. Results of the IVOS analysis are shown in FIGS. 15A and 15B.

Example 16

Figure 16A:
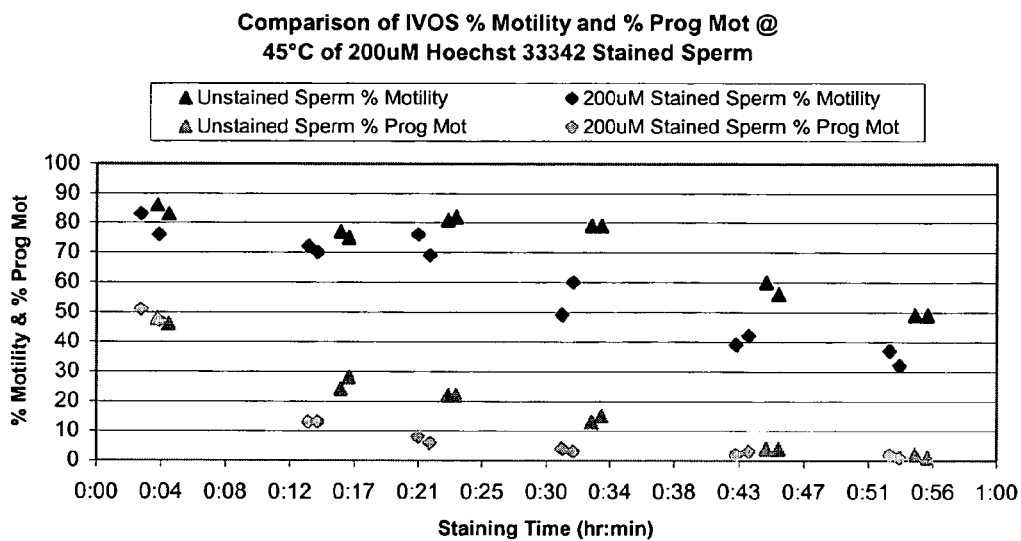
FIGS. 16A-16C graphically depict the results of the study carried out in Example 16 wherein percent motility and percent progressive motility of sperm are measured for sperm unstained, stained with 200 μM Hoechst 33342, stained with 250 μM Hoechst 33342, or stained with 350 μM Hoechst 33342 at 45° C.
Figure 16B:
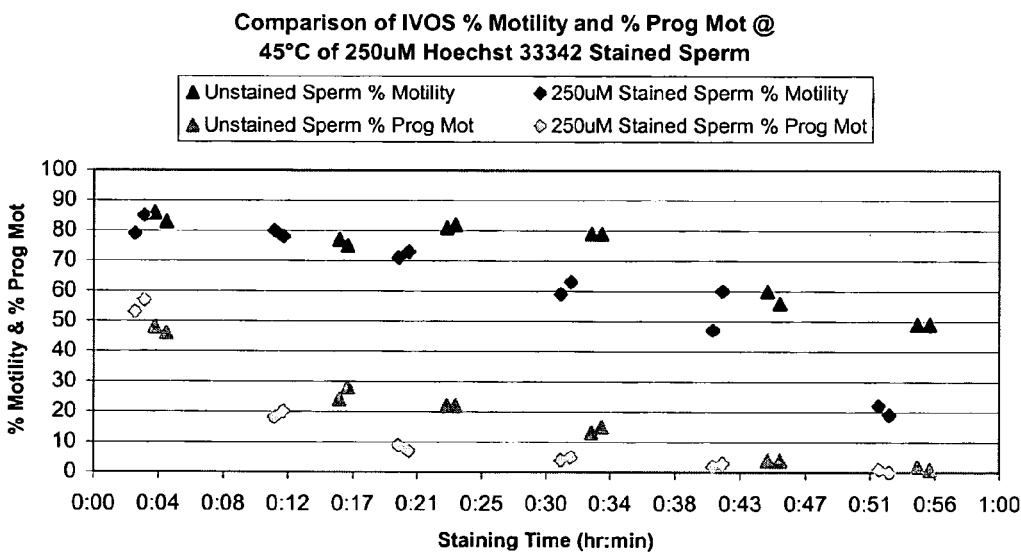
Figure 16C:
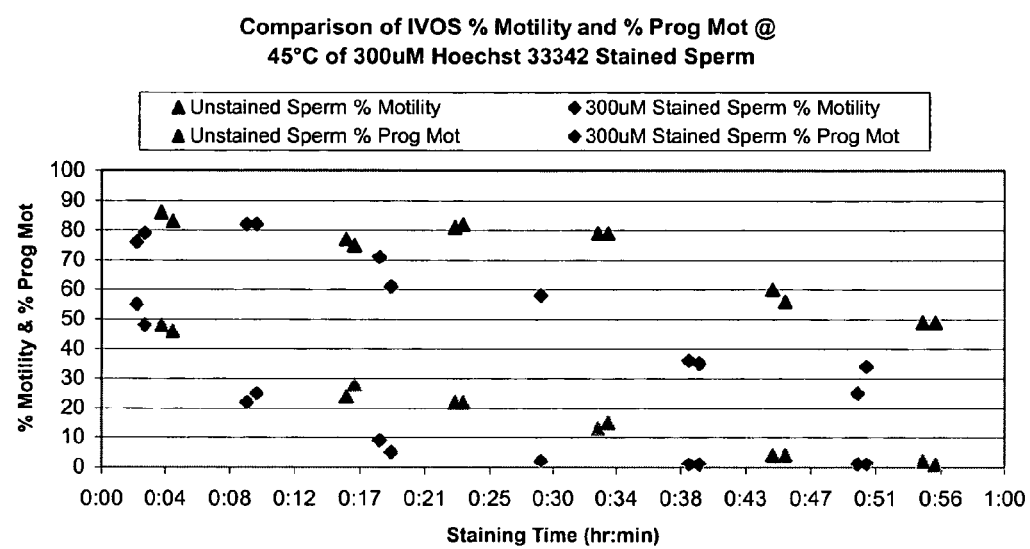

Bull semen was collected, analyzed, suspended in buffer, stained with Hoechst 33342, and analyzed by IVOS as in Example 7 with the following exception. Samples were stained at a concentration of 200 μM, 250 μM, and 300 μM, and each was maintained at a temperature of 45° C. in a water bath. Results of the IVOS analysis are shown in FIGS. 16A-16C.

Example 17

Figure 17A:
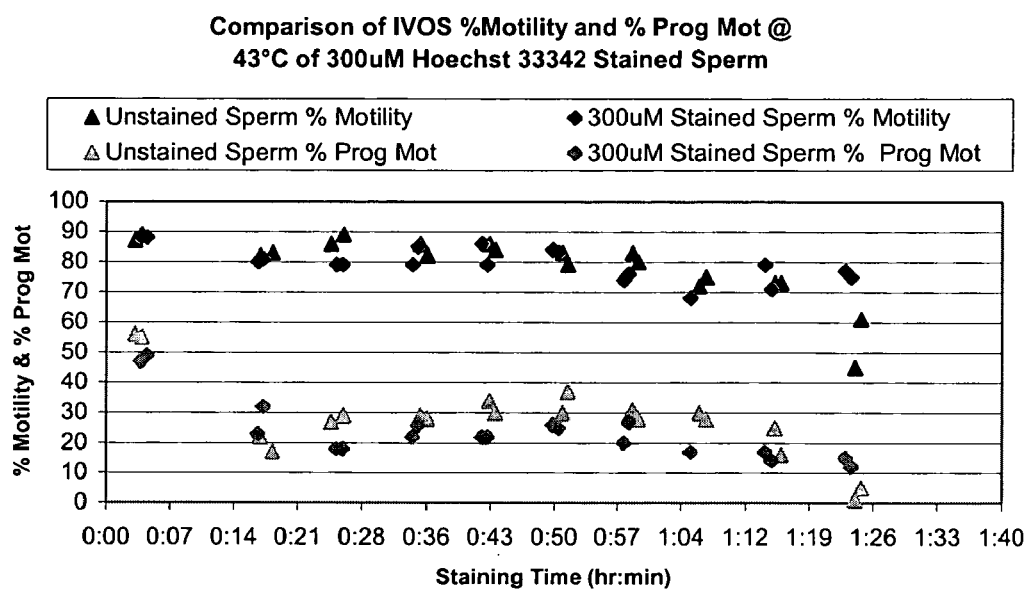
FIGS. 17A-17C graphically depict the results of the study carried out in Example 17 wherein percent motility and percent progressive motility of sperm are measured for sperm unstained, stained with 300 μM Hoechst 33342, stained with 350 μM Hoechst 33342, or stained with 400 μM Hoechst 33342 at 43° C.
Figure 17B:
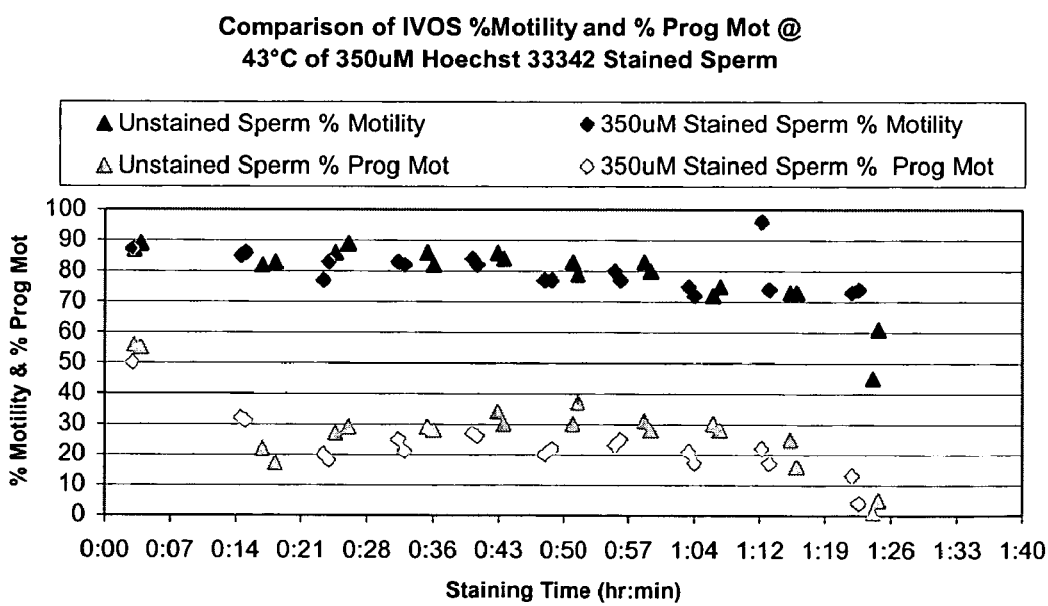
Figure 17C:
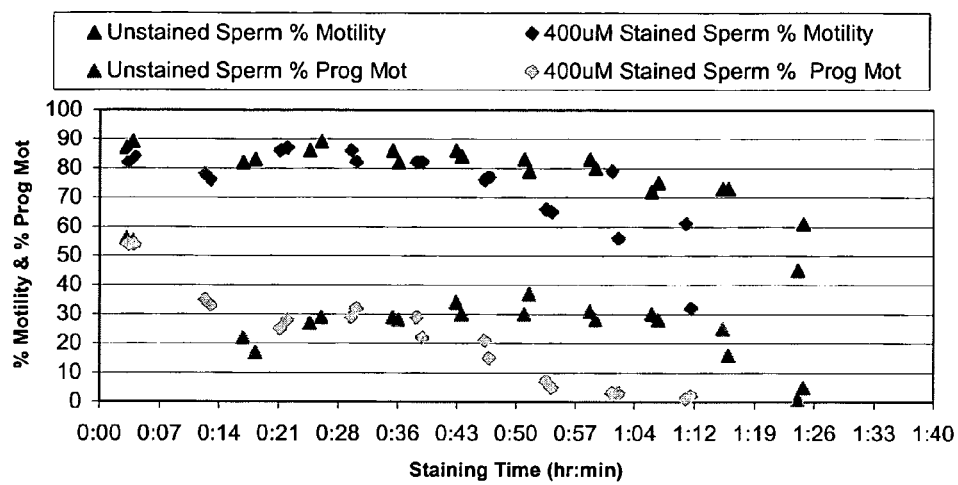

Bull semen was collected, analyzed, suspended in buffer, stained with Hoechst 33342, and analyzed by IVOS as in Example 7 with the following exception. Samples were stained at a concentration rate of 300 μM, 350 μM, and 400 μM, and each was maintained at a temperature of 43° C. in a water bath. Results of the IVOS analysis are shown in FIGS. 17A-17C.

Example 18

Figure 18A:
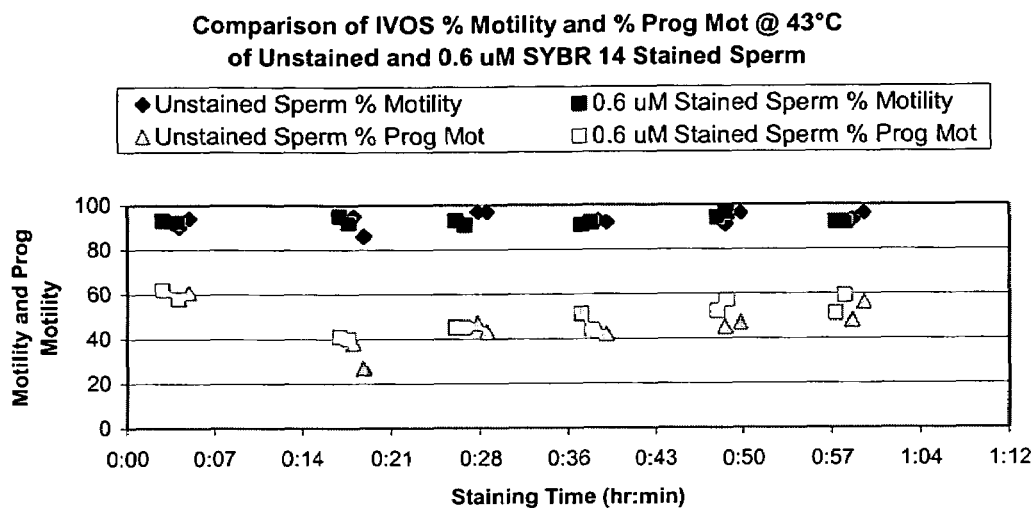
FIGS. 18A-18C graphically depict the results of the study carried out in Example 18 wherein percent motility and percent progressive motility of sperm are measured for sperm unstained, stained with 0.6 μM SYBR 14, stained with 6.0 μM SYBR 14, or stained with 60 μM SYBR at 43° C.
Figure 18B:
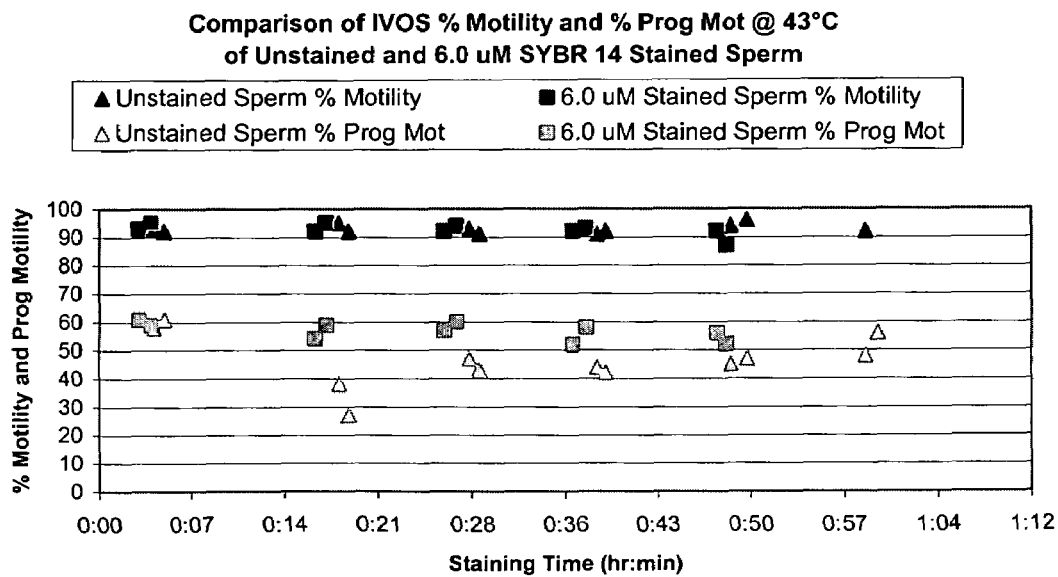
Figure 18C:
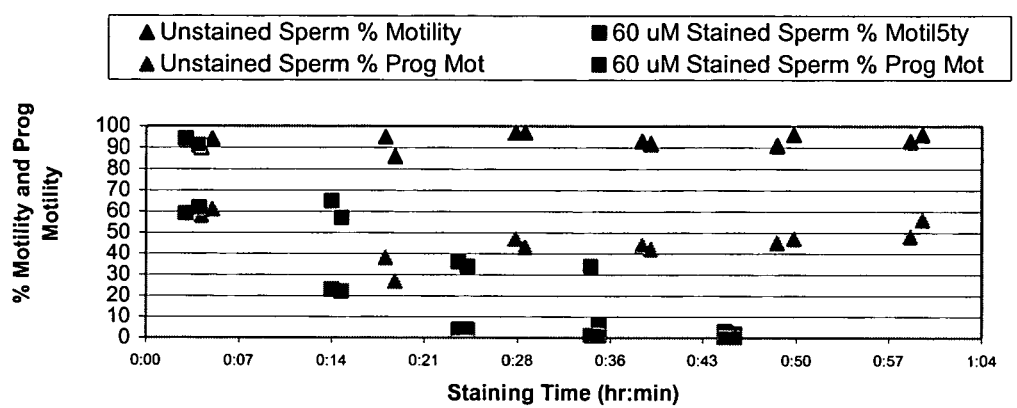

Bull semen was collected from a sexually mature bull using an artificial vagina and the sample transported at 25° C. in a temperature-controlled container to the staining facility. Upon receipt, the semen was analyzed for concentration, visual motility, IVOS motility and progressive motility, pH, and membrane integrity by known analytical methods. Based on the semen concentration, 4×1 mL of 150×10⁶ sperm/mL sperm suspensions were prepared by suspending aliquots of semen in 43° C. TCA buffer at pH 7.35. To three of the samples was added SYBR 14 dye solution to yield the dye concentrations of 0.6 μM, 6 μM, and 60 μM. The suspensions were maintained in a 43° C. water bath. Periodically sample aliquots of 50 μL were transferred to a conical tube and 200 μL of the appropriate temperature TCA buffer added, to yield a final sperm concentration of 30×10⁶ sperm/mL. The samples were immediately analyzed on the IVOS. IVOS results for % Motility and % Progressive Motility (Prog Mot) are shown in FIGS. 18A-18C.

Example 19

Sperm samples were obtained, prepared, stained, and analyzed in the same manner as Example 1 with the exception of the dye and concentrations used. BBC, concentration 100 μM, and SYBR 14, concentration 6 μM, were used to stain the sperm suspensions and the temperatures maintained @ 45° C. in a water bath. Table 7 lists a summary of the concentrations and temperatures used in Example 19.

TABLE 7

| Tube # | Temperature (° C.) | Target concentration of SYBR 14 (μM) | μL 1 mM SYBR 14 to be added to 5 mL of sperm suspension |
|---|---|---|---|
| 1 | 39° C. | 6 μM | 30 μL |
| 2 | 45° C. | 6 μM | 30 μL |
| | | BBC | μL 10 mM BBC |
| 3 | 39° C. | 100 μM | 50 μL |
| 4 | 45° C. | 100 μM | 50 μL |

Figure 19A:
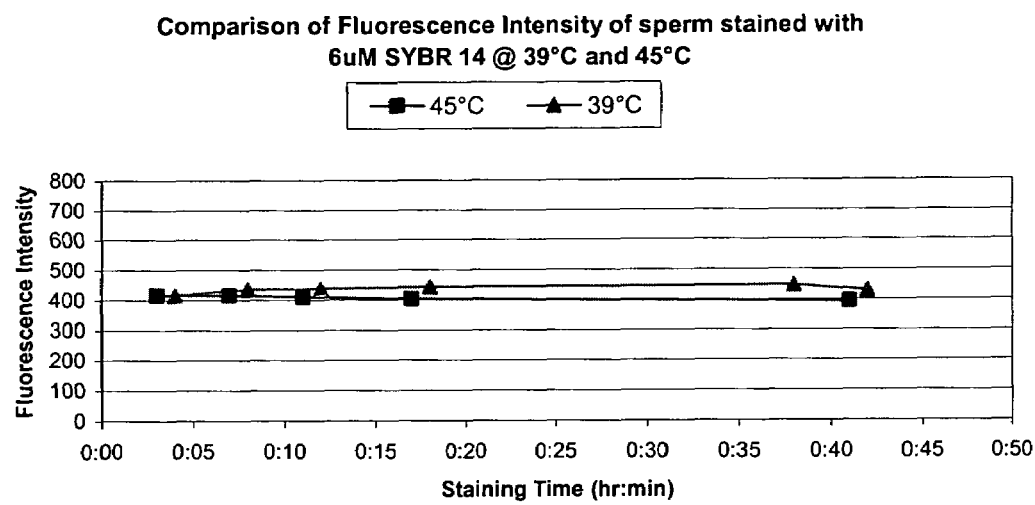
FIGS. 19A-19B graphically depict the results of the study carried out in Example 19 wherein fluorescence intensity of sperm is measured for sperm stained with 100 μM bisbenzimide-BODIPY conjugate (BBC) or 6 μM SYBR 14 at 39° C. and 45° C.
Figure 19B:
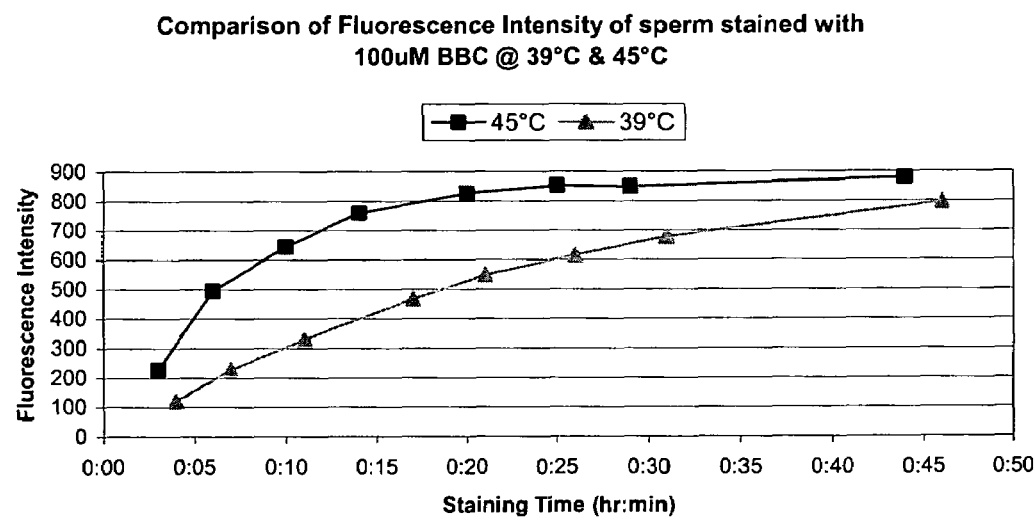

Results of the analysis are summarized in the FIGS. 19A and 19B

Example 20

Figure 20:
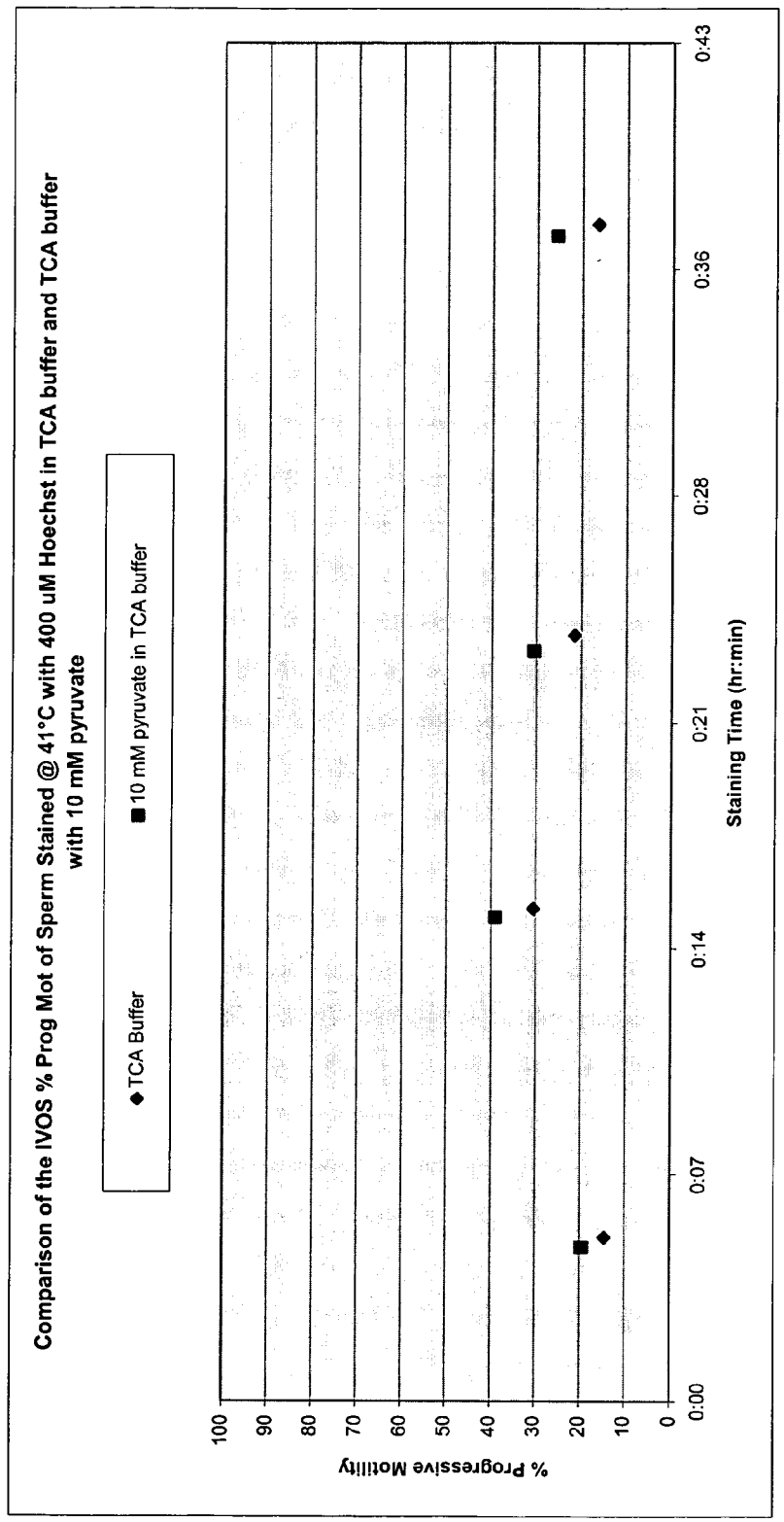
FIG. 20 graphically depicts the results of the study carried out in Example 20 wherein percent progressive motility of sperm is measured for sperm stained with 400 μM Hoechst 33342 dye at 41° C. in either a TCA buffer or a TCA buffer containing 10 mM pyruvate.

Bull semen was collected from a sexually mature bull using an artificial vagina and the sample diluted in 2 parts carbonate buffer for transportation at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. *Theriogenology*, 49 (4): 871-9 (March 1998)). Based on the semen concentration, 1 mL of $150 \times 10^6$ sperm/ml suspension was prepared by removing an aliquot of the carbonate sperm suspension centrifuging the sperm suspension at 500×g for 5 minutes, removing the supernatant and re-suspending the pellet in 41° C. TCA buffer pH 7.3. An additional 1 mL of $150 \times 10^6$ sperm/ml was prepared by suspending an aliquot of semen in 41° C. TCA-buffer containing 10 mM pyruvate at pH 7.3. To the sperm suspensions, aliquots of a 10 mM Hoechst solution in water were added to yield the dye concentration of 400 μM Hoechst. The sperm suspensions were maintained in a 41° C. water bath for the duration of the staining period. Sperm suspensions were analyzed by removing a 50 μL aliquot from the staining sperm suspension, adding 200 μL of the same buffer at the same temperature and analyzing by IVOS to measure % progressive motility (% Prog Mot). Results of the IVOS analysis are summarized in FIG. 20.

Example 21

Figure 21:
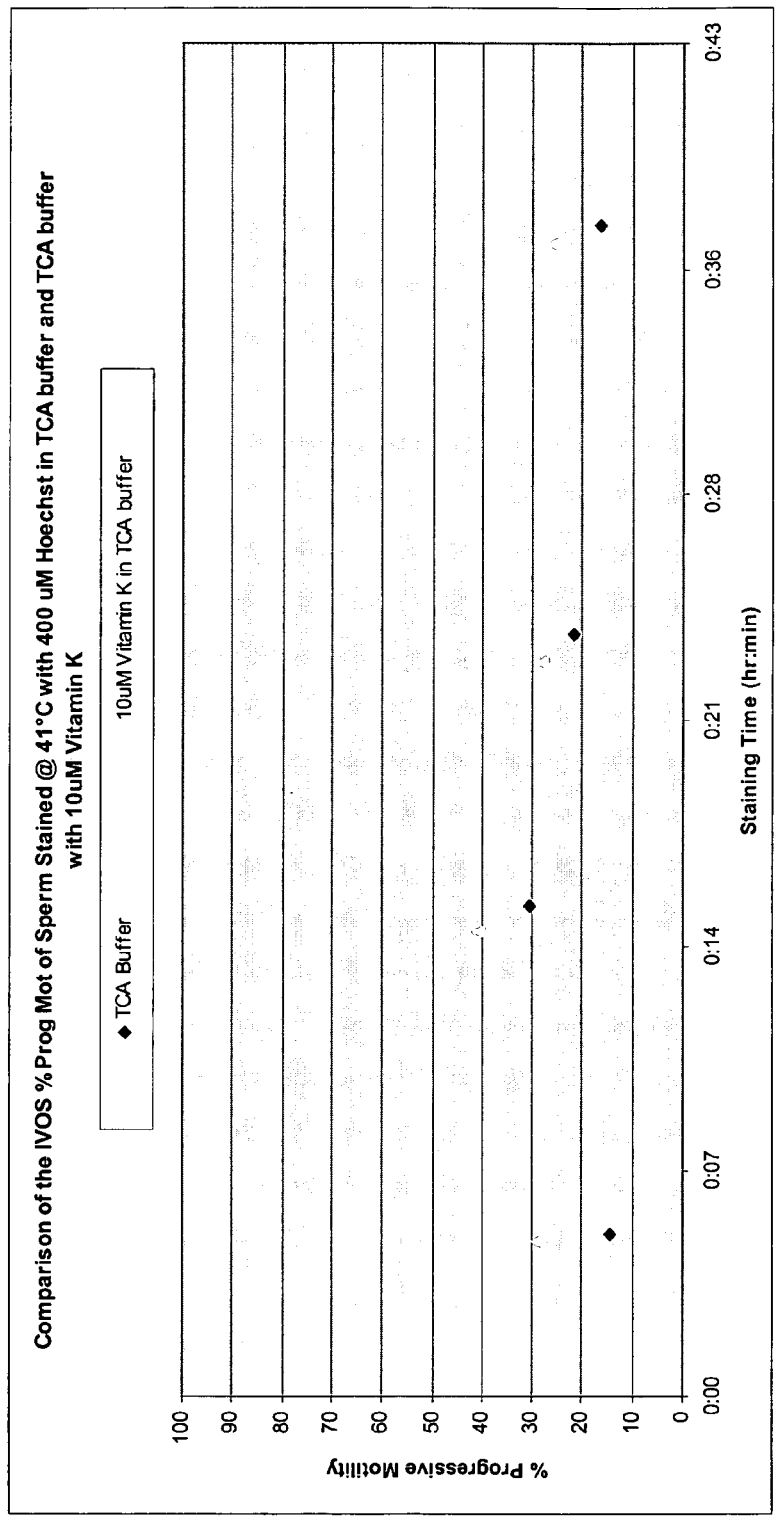
FIG. 21 graphically depicts the results of the study carried out in Example 21 wherein percent progressive motility of sperm is measured for sperm stained with 400 μM Hoechst 33342 dye at 41° C. in either a TCA buffer or a TCA buffer containing 10 μM vitamin K.

Sperm samples were obtained and prepared in the same manner as in Example 20 with the following exception. The buffer used to suspend the sperm for staining and IVOS analysis were TCA and TCA containing 10 μM Vitamin K. Results of the IVOS analysis are summarized in FIG. 21

Example 22

Figure 22:
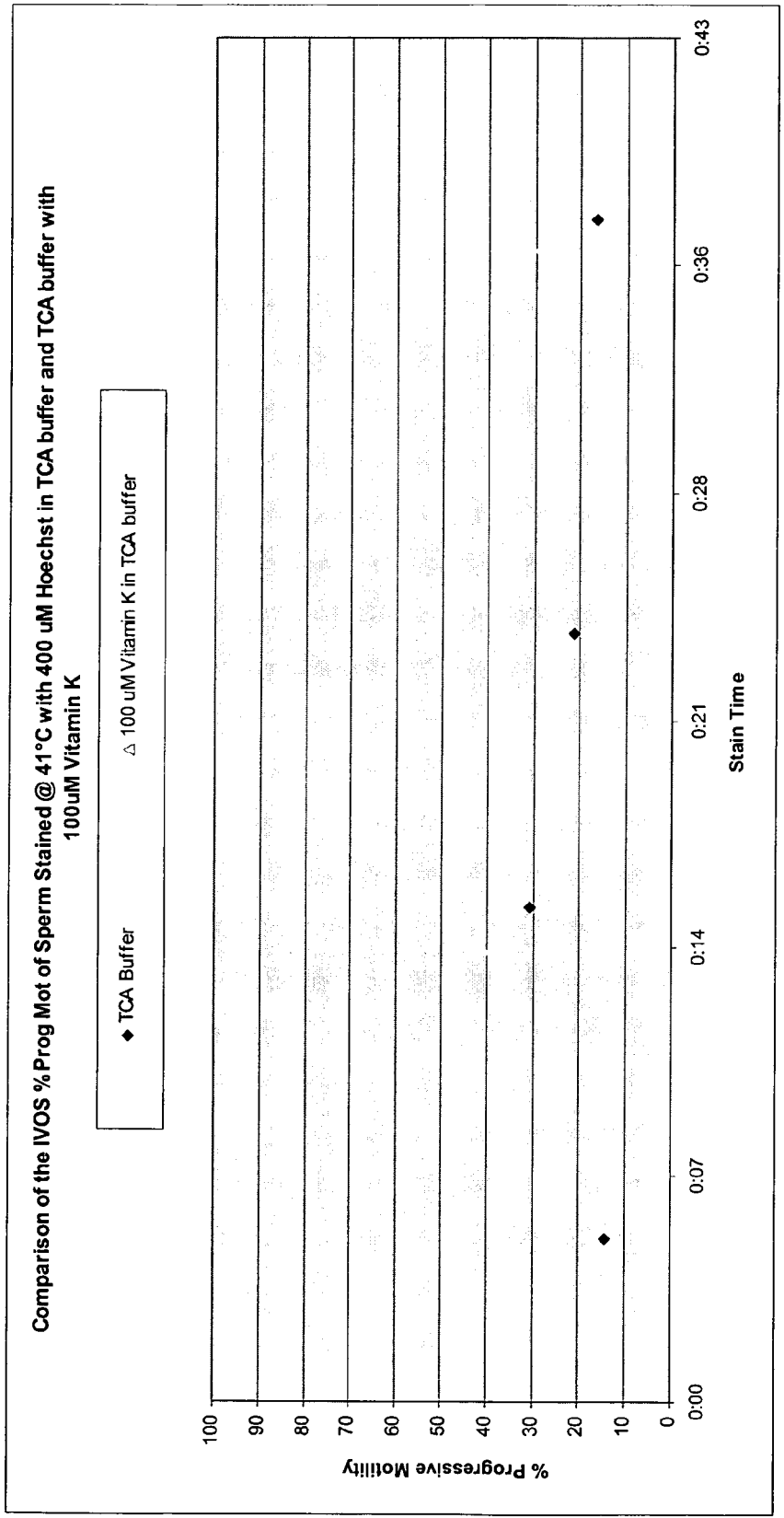
FIG. 22 graphically depicts the results of the study carried out in Example 22 wherein percent progressive motility of sperm is measured for sperm stained with 400 μM Hoechst 33342 dye at 41° C. in either a TCA buffer or a TCA buffer containing 100 μM vitamin K.

Sperm samples were obtained and prepared in the same manner as in Example 20 with the following exception. The buffer used to suspend the sperm for staining and IVOS analysis were TCA and TCA containing 100 uM Vitamin K. Results of the IVOS analysis are summarized in FIG. 22.

Example 23

Figure 23:
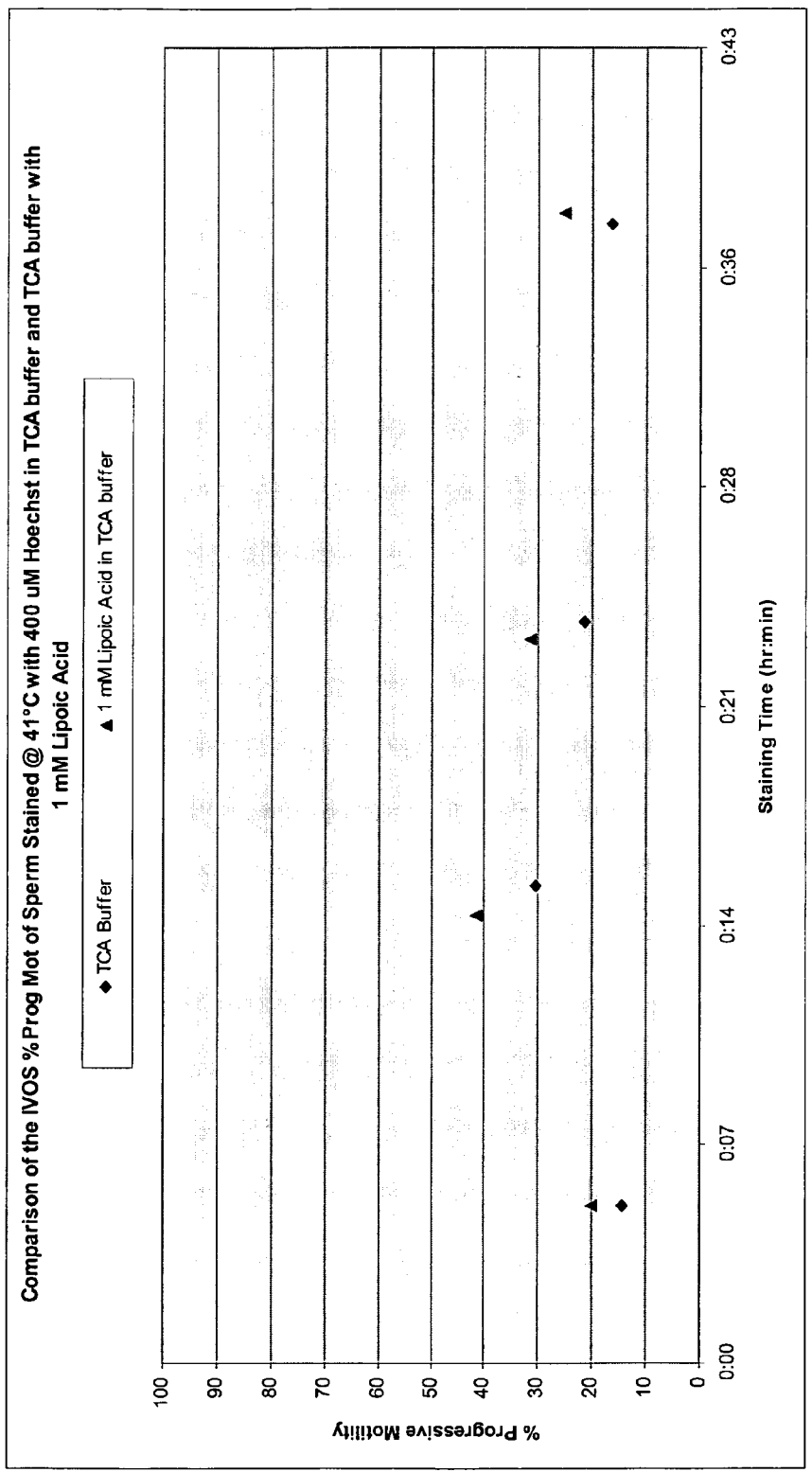
FIG. 23 graphically depicts the results of the study carried out in Example 23 wherein percent progressive motility of sperm is measured for sperm stained with 400 μM Hoechst 33342 dye at 41° C. in either a TCA buffer or a TCA buffer containing 1 mM lipoic acid.

Sperm samples were obtained and prepared in the same manner as in Example 20 with the following exception. The buffers used to suspend the sperm for staining and IVOS analysis were TCA and TCA containing 1 mM Lipoic Acid. Results of the IVOS analysis are summarized in FIG. 23.

Example 24

Bull semen was collected from a sexually mature bull using an artificial vagina and transported at 25° C. in a temperature-controlled container to the staining facility. Upon receipt, the semen was analyzed for concentration, motility and progressive motility by the Hamilton-Thorn Motility Analyzer (IVOS), according to standard and well known procedures (Farrell et al. Theriogenology, 49 (4): 871-9 (March 1998)). Based on the semen concentration, several tubes of $450 \times 10^6$ sperm/ml suspensions were prepared by suspending semen in either a TCA buffer or a carbonate based inhibitor. Table II. below illustrates the compositions and staining conditions used.

TABLE III

| Sample Name | Buffer | pH | Conc (uM) Hoechst | Temperature (° C.) |
|---|---|---|---|---|
| 10 mM pyr TCA | 10 mM pyruvate in TCA | 7.3 | 300 μM | 41° C. |
| Carbonate 6.2 | Carbonate based inhibitor, pH 6.2 | 6.2 | 300 μM | 41° C. |
| Carbonate 7.3 | Carbonate based inhibitor, pH 7.3 | 7.3 | 300 μM | 41° C. |

Figure 24:
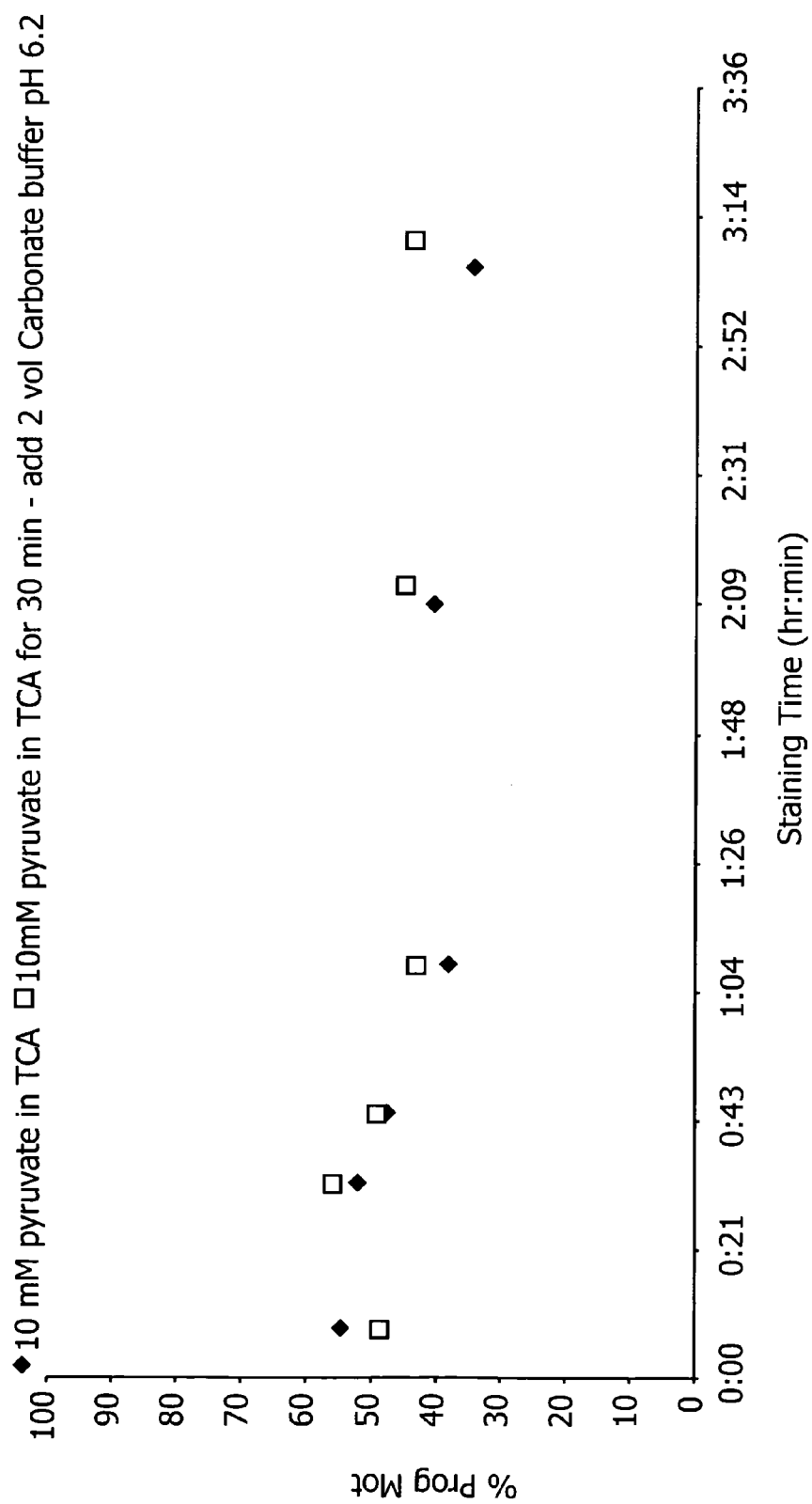
FIG. 24 graphically depicts the results of the study carried out in Example 24 wherein percent progressive motility of sperm cells is measured for sperm cells stained with 300 μM Hoechst 33342 dye at 41° C. in TCA containing 10 mM pyruvate and then diluted 1 to 3 with either TCA containing 10 mM pyruvate or a carbonate-based inhibitor at pH 6.2.
Figure 25:
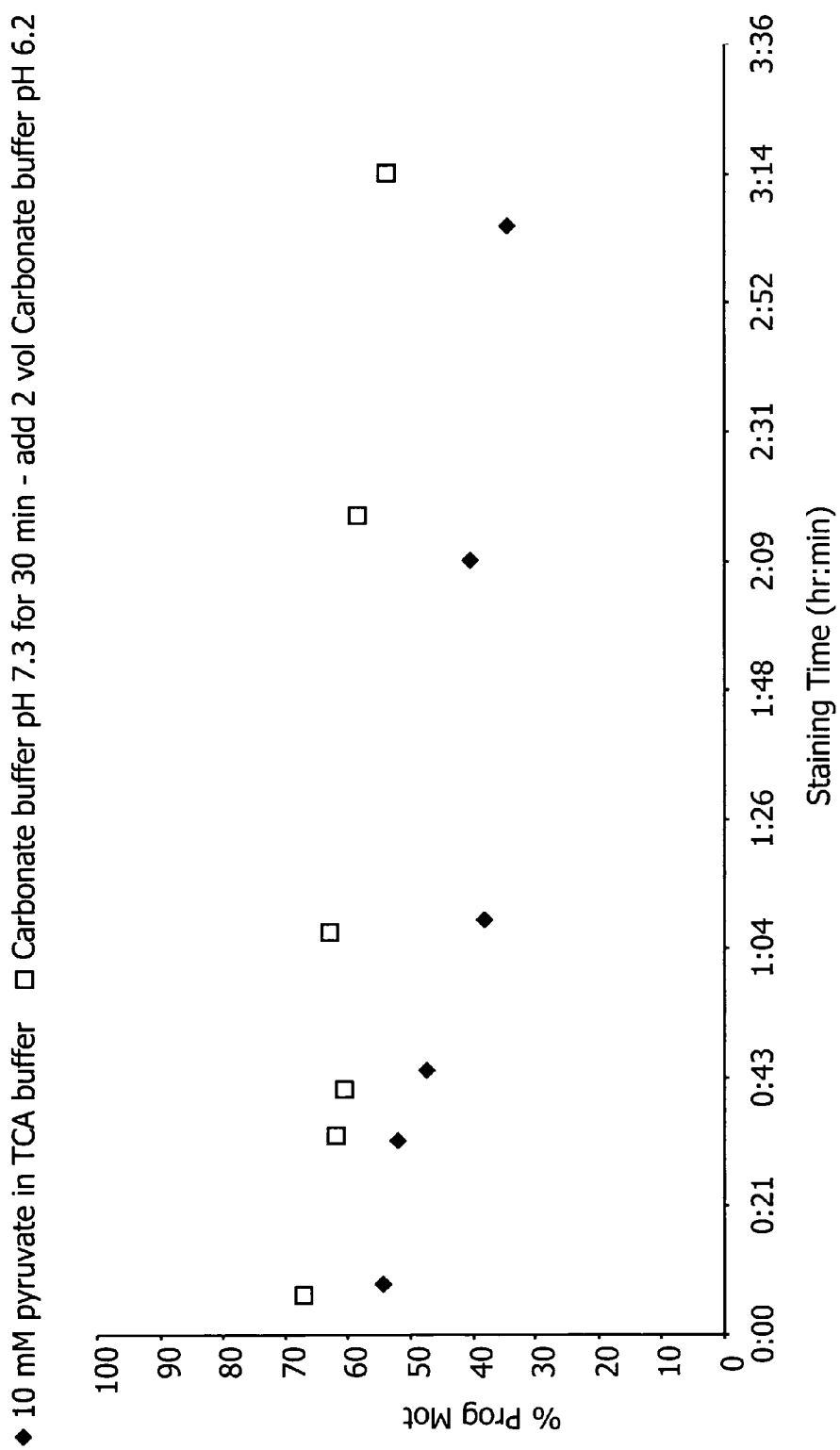
FIG. 25 graphically depicts the results of the study carried out in Example 24 wherein percent progressive motility of sperm cells is measured for sperm cells stained with 300 μM Hoechst 33342 dye at 41° C. in (1) TCA containing 10 mM pyruvate and diluted 1 to 3 with the same or (2) a carbonate-based buffer at pH 7.3 and diluted 1 to 3 with carbonate-based inhibitor at pH 6.2.
Figure 26:
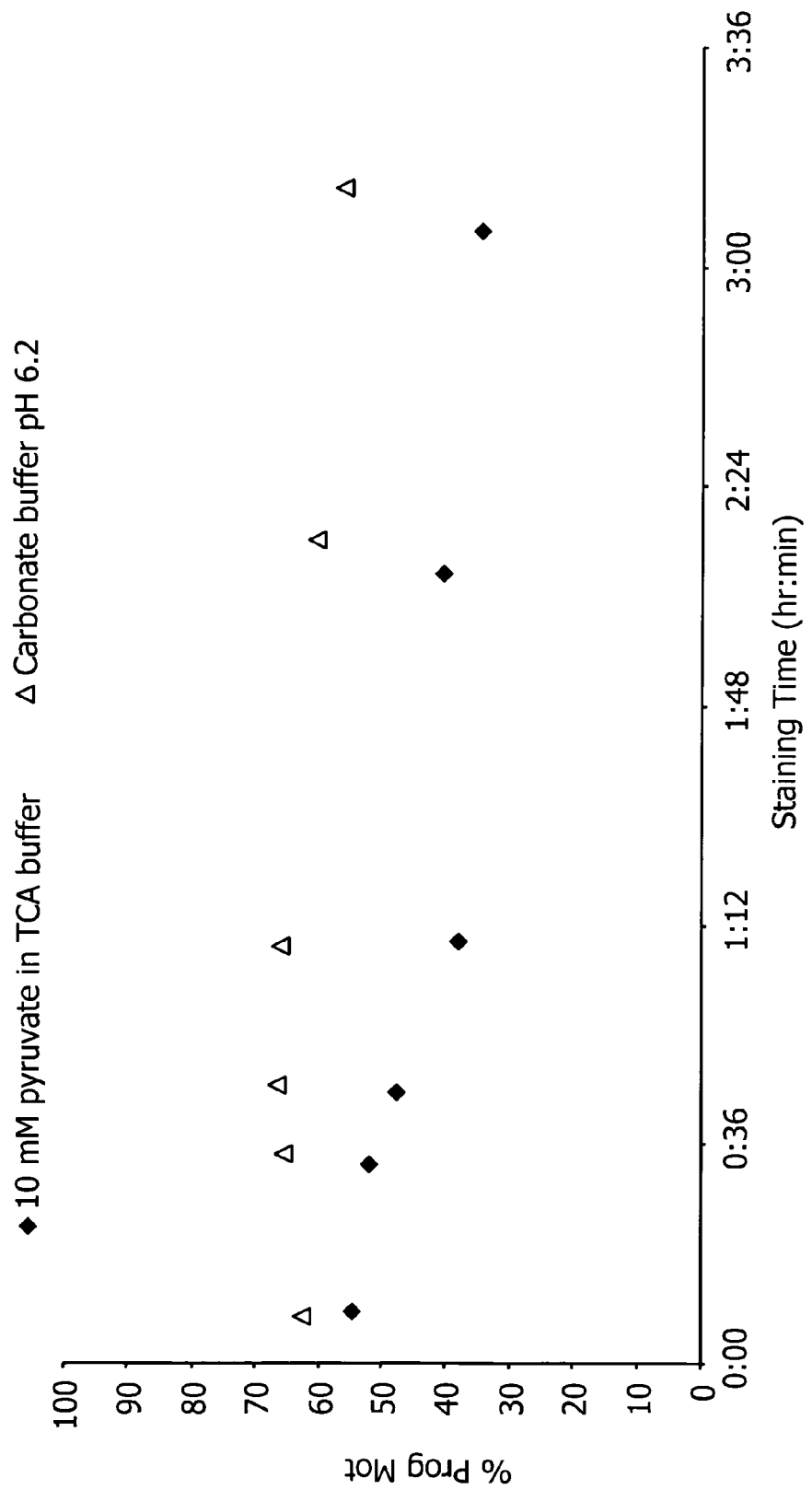
FIG. 26 graphically depicts the results of the study carried out in Example 24 wherein percent progressive motility of sperm cells is measured for sperm cells stained with 300 μM Hoechst 33342 dye at 41° C. in TCA containing 10 mM pyruvate or a carbonate-based inhibitor at pH 6.2.

To the sperm suspensions, aliquots of a 10 mM Hoechst solution in water were added to yield a concentration of 300 μM Hoechst. The sperm suspensions were maintained in a 41° C. water bath for 30 minutes, and then diluted to $150 \times 10^6$ sperm/ml with 10 mM pyruvate in TCA or a carbonate-based inhibitor at pH 6.2 as specifically indicated in each figure to dilute to a concentration typical for sorting. Sperm suspensions were analyzed by removing a 50 μL aliquot from the stained and diluted sperm suspension at the time period designated within each figure and adding 200 μL of 25° C. 10 mM pyruvate in TCA at pH 7.3 to initiate the reversal of the quiescence, allowing at least a five minute equilibration period, and analyzing by IVOS to measure the percent progressive motility. Comparisons of the IVOS percent progressive motilities are seen in FIGS. 24-26.

What is claimed is:

1. A process for staining sperm cells, the process comprising forming a staining mixture containing intact viable sperm cells and a DNA selective fluorescent dye, and subjecting the staining mixture to a temperature between 41° C. and 47° C. for a period of time sufficient to allow the dye to bind to the DNA without significantly impacting viability of the stained cells.

2. The process of claim 1, wherein the dye is a UV excitable or a visible light excitable dye.

3. The process of claim 2, wherein the dye is selected from the group consisting of a bisbenzimide, SYBR-14, and a conjugate, an analog, or a derivative thereof.

4. The process of claim 3, wherein the dye is selected from the group consisting of Hoechst 33342, Hoechst 33258, SYBR-14, and 6-{[3-((2Z)-2-{[1-(difluoroboryl)-3,5-dimethyl-1H-pyrrol-2-yl]methylene}-2H-pyrrol-5-yl)propanoyl]amino}-N-[3-(methyl{3-[({4-[6-(4-methylpiperazin-1-yl)-1H,3'H-2,5'-bibenzimidazol-2'-yl]phenoxy}acetyl)amino]propyl}amino)propyl]hexanamide.

5. The process of claims 1, wherein the staining mixture is subjected to the temperature for a period of time sufficient to allow the dye to bind the DNA such that X and Y bearing sperm cells can be differentially sorted based upon fluorescence.

6. The process of claim 5, wherein the period of time is from about 1 minute to about 160 minutes.

7. The process of claim 5, wherein the period of time is less than about 60 minutes.

8. The process of claim 5, wherein the period of time is less than about 30 minutes.

9. The process of claim 5, wherein the dye concentration is from about 0.1 µM to about 1000 µM.

10. The process of claim 9, wherein the dye concentration is from about 100 µM to about 600 µM.

11. The process of claim 5, wherein the staining mixture is subjected to a temperature of between 41° C. and 45° C.

12. The process of claim 5, wherein the staining mixture is subjected to a temperature of between 42° C. and 45° C.

13. The process of claim 5, wherein the staining mixture is subjected to a temperature of 41° C.

14. The process of claim 5, wherein the staining mixture is subjected to a temperature of 45° C.

15. The process of claim 5, wherein the staining mixture is subjected to a temperature of 43° C.

16. The process of claim 1, wherein the step of forming a staining mixture comprises combining a buffer with the sperm cells.

17. The process of claim 16, wherein the buffer is combined with the sperm cells to form a sperm suspension, and the sperm suspension is combined with a DNA selective dye to form the staining mixture.

18. The process of claim 1, wherein the step of forming a staining mixture comprises combining a buffer with a DNA selective dye to form a buffered dye solution, and combining the buffered dye solution with the sperm cells to form the staining mixture.

19. The process of claim 1, further comprising the step of combining a quencher with the staining mixture.

20. The process of claim 19, wherein the quencher is selected from the group consisting of FD&C #40 and propidium iodide.

21. The process of claim 20, wherein the quencher is FD&C #40.

22. The process of claim 20, wherein the quencher is FD&C #40 and the dye is Hoechst 33342.

23. The process of claim 20, wherein the quencher is propidium iodide and the dye is SYBR-14.

24. The process of claim 1, wherein the staining mixture further contains a motility inhibitor.

25. The process of claim 1, wherein the step of forming a staining mixture comprises combining a motility inhibitor with the sperm cells to form an inhibited sperm suspension, and combining the inhibited sperm suspension with a DNA selective dye to form the staining mixture.

26. The process of claim 25, wherein the motility inhibitor comprises a carbonate based motility inhibitor.

27. The process of claim 26, wherein the carbonate based motility inhibitor comprises $NaHCO_3$, $KHCO_3$, and $C_6H_8O_7 \cdot H_2O$.

28. The process of claim 27, wherein the carbonate based motility inhibitor comprises 0.097 moles/L of $NaHCO_3$, 0.173 moles/L of $KHCO_3$, 0.090 moles/L $C_6H_8O_7 \cdot H_2O$ in water.

29. The process of claim 1, wherein the staining mixture further contains a composition which regulates oxidation/reduction reactions intracellularly or extracellularly.

30. The process of claim 29, wherein the composition which regulates oxidation/reduction reactions intracellularly or extracellularly is selected from the group consisting of pyruvate, vitamin K, lipoic acid, glutathione, flavins, quinones, superoxide dismutase, and superoxide dismutase mimics.

31. The process of claim 30, wherein the composition which regulates oxidation/reduction reactions intracellularly or extracellularly is selected from the group consisting of pyruvate, vitamin K, and lipoic acid.

32. The process of claim 31, wherein the composition which regulates oxidation/reduction reactions intracellularly or extracellularly comprises pyruvate at a concentration from about 0.5 µM to about 50 mM.

33. The process of claim 32, wherein the composition which regulates oxidation/reduction reactions intracellularly or extracellularly comprises pyruvate at a concentration from about 10 mM to about 15 mM.

34. The process of claim 33, wherein the composition which regulates oxidation/reduction reactions intracellularly or extracellularly comprises pyruvate at a concentration of about 10 mM.

35. The process of claim 31, wherein the composition which regulates oxidation/reduction reactions intracellularly or extracellularly comprises vitamin K at a concentration of about 1 µM to about 100 µM.

36. The process of claim 35, wherein the composition which regulates oxidation/reduction reactions intracellularly or extracellularly comprises vitamin K at a concentration of about 100 µM.

37. The process of claim 31, wherein the composition which regulates oxidation/reduction reactions intracellularly or extracellularly comprises lipoic acid at a concentration of about 0.1 mM to about 1.0 mM.

38. The process of claim 31, wherein the composition which regulates oxidation/reduction reactions intracellularly or extracellularly comprises lipoic acid at a concentration of about 1.0 mM.

* * * * *